US009726632B2

(12) United States Patent
Wu

(10) Patent No.: US 9,726,632 B2
(45) Date of Patent: Aug. 8, 2017

(54) IDENTIFYING IONIZABLE SPECIES WITH VOLTAMMETRIC DUTY CYCLES

(71) Applicant: Bayer HealthCare LLC, Whippany, NJ (US)

(72) Inventor: Huan-Ping Wu, Granger, IN (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 0 days.

(21) Appl. No.: 14/958,562

(22) Filed: Dec. 3, 2015

(65) Prior Publication Data

US 2016/0084791 A1     Mar. 24, 2016

Related U.S. Application Data

(60) Continuation of application No. 14/513,867, filed on Oct. 14, 2014, now Pat. No. 9,228,978, which is a
(Continued)

(51) Int. Cl.
*G01N 27/327* (2006.01)
*G01N 27/48* (2006.01)

(52) U.S. Cl.
CPC ..... *G01N 27/3272* (2013.01); *G01N 27/3271* (2013.01); *G01N 27/3273* (2013.01); *G01N 27/48* (2013.01)

(58) Field of Classification Search
None
See application file for complete search history.

(56) References Cited

U.S. PATENT DOCUMENTS

| 4,897,162 A | 1/1990 | Lewandowski |
| 5,243,516 A | 9/1993 | White |

(Continued)

FOREIGN PATENT DOCUMENTS

| WO | WO96-14026 | 5/1996 |
| WO | WO01-57510 | 8/2001 |

(Continued)

OTHER PUBLICATIONS

International Searching Authority, "International Search Report for PCT/US2009/050244", Nov. 18, 2009, Publisher: World Intellectual Property Organization, Published in: WIPO.
(Continued)

*Primary Examiner* — J. Christopher Ball
(74) *Attorney, Agent, or Firm* — Nixon Peabody LLP

(57) ABSTRACT

A sensor system including devices and methods for determining the concentration of an analyte in a sample is described. Input signals including amperometric and voltammetric duty cycles of excitations and relaxations may provide a shorter analysis time and/or improve the accuracy and/or precision of the analysis. The disclosed system may reduce analysis errors, thus improving measurement performance, by adjusting the potential and/or scan rate in response to output currents obtained from voltammetric scans. The disclosed system also may determine the concentration of more than one ionizable species in the sample by adjusting the potential and/or scan rate in response to output currents obtained from voltammetric scans. The multiple, determined concentrations may be used to determine the concentration of multiple analytes or to correct the concentration determined for an analyte, thus improving the measurement performance of the system.

20 Claims, 24 Drawing Sheets

Related U.S. Application Data division of application No. 13/552,954, filed on Jul. 19, 2012, now Pat. No. 8,871,070, which is a division of application No. 12/501,107, filed on Jul. 10, 2009, now Pat. No. 8,262,899.

(60) Provisional application No. 61/079,616, filed on Jul. 10, 2008.

(56) References Cited

U.S. PATENT DOCUMENTS

| | | |
|---|---|---|
| 5,393,615 A | 2/1995 | Corey |
| 5,429,735 A | 7/1995 | Johnson |
| 5,498,542 A | 3/1996 | Corey |
| 5,520,786 A | 5/1996 | Bloczynski |
| 5,620,579 A | 4/1997 | Genshaw |
| 5,653,863 A | 8/1997 | Genshaw |
| 5,708,247 A | 1/1998 | McAleer |
| 5,807,375 A | 9/1998 | Gross |
| 5,942,102 A | 8/1999 | Hodges |
| 5,951,836 A | 9/1999 | McAleer |
| 6,153,069 A | 11/2000 | Pottgen |
| 6,251,260 B1 | 6/2001 | Heller |
| 6,275,717 B1 | 8/2001 | Gross |
| 6,413,411 B1 | 7/2002 | Pottgen |
| 6,576,117 B1 | 6/2003 | Iketaki |
| 6,824,670 B2 | 11/2004 | Tokunaga |
| 7,018,843 B2 | 3/2006 | Heller |
| 7,122,111 B2 | 10/2006 | Tokunaga |
| 7,338,639 B2 | 3/2008 | Burke |
| 7,351,323 B2 | 4/2008 | Iketaki |
| 8,088,272 B2 | 1/2012 | Deng |
| 8,101,062 B2 | 1/2012 | Deng |
| 8,105,478 B2 | 1/2012 | Barlag |
| 2003/0113933 A1 | 6/2003 | Jansson |
| 2003/0146110 A1 | 8/2003 | Karinka |
| 2003/0178322 A1 | 9/2003 | Iyengar |
| 2004/0045821 A1 | 3/2004 | Cui |
| 2005/0049473 A1 | 3/2005 | Desai |
| 2006/0063218 A1 | 3/2006 | Bartkowiak |
| 2006/0074564 A1 | 4/2006 | Bartkowiak |
| 2006/0085137 A1 | 4/2006 | Bartkowiak |
| 2006/0191787 A1 | 8/2006 | Wang |
| 2007/0074977 A1 | 4/2007 | Guo |
| 2008/0011606 A1 | 1/2008 | Zhang |
| 2008/0102441 A1 | 5/2008 | Chen |
| 2008/0149480 A1 | 6/2008 | Bell |
| 2009/0026094 A1 | 1/2009 | Deng |

FOREIGN PATENT DOCUMENTS

| | | |
|---|---|---|
| WO | WO2004-053476 | 6/2004 |
| WO | WO2007-013915 | 2/2007 |
| WO | WO2007-040913 | 4/2007 |

OTHER PUBLICATIONS

Bard, et al. "Electrochemical Methods Fundamentals and Application", 1980, pp. 236-241.

IDENTIFYING IONIZABLE SPECIES WITH VOLTAMMETRIC DUTY CYCLES

CROSS-REFERENCE TO RELATED APPLICATIONS

This application is a continuation of U.S. Nonprovisional application Ser. No. 14/513,867, filed Oct. 14, 2014, entitled "Identifying Ionizable Species with Voltammetric Duty Cycles", now allowed, which is a divisional of U.S. Nonprovisional application Ser. No. 13/552,954, filed Jul. 19, 2012, entitled "Systems, Methods, and Devices Including Amperometric and Voltammetric Duty Cycles", now U.S. Pat. No. 8,871,070, which is a divisional of U.S. Nonprovisional application Ser. No. 12/501,107, filed Jul. 10, 2009, entitled "Systems and Methods Including Amperometric and Voltammetric Duty Cycles", now U.S. Pat. No. 8,262,899, which claims the benefit of U.S. Provisional Application No. 61/079,616 entitled "Systems and Methods Including Amperometric and Voltammetric Duty Cycles" filed Jul. 10, 2008, each of which is hereby incorporated by reference herein in its entirety.

BACKGROUND

Biosensor systems provide an analysis of a biological fluid, such as whole blood, serum, plasma, urine, saliva, interstitial, or intracellular fluid. Typically, biosensor systems have a measurement device that analyzes a sample contacting a sensor strip. The sample is typically in liquid form and in addition to being a biological fluid, may be the derivative of a biological fluid, such as an extract, a dilution, a filtrate, or a reconstituted precipitate. The analysis performed by the system determines the presence and/or concentration of one or more analytes, such as alcohol, glucose, uric acid, lactate, cholesterol, bilirubin, free fatty acids, triglycerides, proteins, ketones, phenylalanine, or enzymes, in the biological fluid. The analysis may be useful in the diagnosis and treatment of physiological abnormalities. For example, a diabetic individual may use a biosensor system to determine the glucose level in whole blood for adjustments to diet and/or medication.

Biosensor systems may be designed to analyze one or more analytes in the same or in different samples and may use different sample volumes. Some systems may analyze a single drop of whole blood, such as from 0.25-15 microliters (µL) in volume. Biosensor systems may be implemented using bench-top, portable, and like measurement devices. Portable measurement devices may be hand-held and allow for the identification and/or quantification of one or more analytes in a sample. Examples of portable measurement devices include the Breeze II® and Contour® meters of Bayer HealthCare Diabetes Care in Tarrytown, N.Y., while examples of bench-top measurement devices include the Electrochemical Workstation available from CH Instruments in Austin, Tex. Systems providing shorter analysis times, while supplying the desired accuracy and/or precision, provide a substantial benefit to the user.

In electrochemical biosensor systems, the analyte concentration is determined from an electrical signal generated by an oxidation/reduction or redox reaction of a measurable species. The measurable species may be ionized analyte or an ionized species responsive to the analyte when an input signal is applied to the sample. The input signal may be applied as a single pulse or in multiple pulses, sequences, or cycles. An oxidoreductase, such as an enzyme or similar species, may be added to the sample to enhance the electron transfer from a first species to a second species during the redox reaction. The enzyme or similar species may react with a single analyte, thus providing specificity to a portion of the generated output signal. Examples of some specific oxidoreductases and corresponding analytes are given below in Table I.

TABLE I

| Oxidoreductase | Analyte |
| --- | --- |
| Glucose dehydrogenase | β-glucose |
| Glucose oxidase | β-glucose |
| Cholesterol esterase; cholesterol oxidase | Cholesterol |
| Lipoprotein lipase; glycerol kinase; glycerol-3-phosphate oxidase | Triglycerides |
| Lactate oxidase; lactate dehydrogenase; diaphorase | Lactate |
| Pyruvate oxidase | Pyruvate |
| Alcohol oxidase | Alcohol |
| Bilirubin oxidase | Bilirubin |
| Uricase | Uric acid |
| Glutathione reductase | NAD(P)H |
| Carbon monoxide oxidoreductase | Carbon monoxide |

A mediator may be used to maintain the oxidation state of the enzyme. In maintaining the oxidation state of the enzyme, the mediator is ionized and may serve as a measurable species responsive to the analyte. Table II, below, provides some conventional combinations of enzymes and mediators for use with specific analytes.

TABLE II

| Analyte | Enzyme | Mediator |
| --- | --- | --- |
| Glucose | Glucose Oxidase | Ferricyanide |
| Glucose | Glucose Dehydrogenase | Ferricyanide |
| Cholesterol | Cholesterol Oxidase | Ferricyanide |
| Lactate | Lactate Oxidase | Ferricyanide |
| Uric Acid | Uricase | Ferricyanide |
| Alcohol | Alcohol Oxidase | Phenylenediamine |

The mediator may be a one electron transfer mediator or a multi-electron transfer mediator. One electron transfer mediators are chemical moieties capable of taking on one additional electron during the conditions of the electrochemical reaction. One electron transfer mediators include compounds, such as 1,1'-dimethyl ferrocene, ferrocyanide and ferricyanide, and ruthenium(III) and ruthenium(II) hexaamine. Multi-electron transfer mediators are chemical moieties capable of taking on more-than-one electron during the conditions of the reaction. Multi-electron transfer mediators include two electron transfer mediators, such as the organic quinones and hydroquinones, including phenanthroline quinone; phenothiazine and phenoxazine derivatives; 3-(phenylamino)-3H-phenoxazines; phenothiazines; and 7-hydroxy-9,9-dimethyl-9H-acridin-2-one and its derivatives. Two electron transfer mediators also include the electro-active organic molecules described in U.S. Pat. Nos. 5,393,615; 5,498,542; and 5,520,786.

Two electron transfer mediators include 3-phenylimino-3H-phenothiazines (PIPT) and 3-phenylimino-3H-phenoxazines (PIPO). Two electron mediators also include the carboxylic acid or salt, such as ammonium salts, of phenothiazine derivatives. Two electron mediators further include (E)-2-(3H-phenothiazine-3-ylideneamino)benzene-1,4-disulfonic acid (Structure I), (E)-5-(3H-phenothiazine-3-ylideneamino)isophthalic acid (Structure II), ammonium (E)-3-(3H-phenothiazine-3-ylideneamino)-5-carboxybenzoate (Structure III), and combinations thereof. The structural formulas of these mediators are presented below. While only the di-acid form of the Structure I mediator is shown, mono- and di-alkali metal salts of the acid are included. The sodium salt of the acid may be used for the Structure I mediator. Alkali-metal salts of the Structure II mediator also may be used.

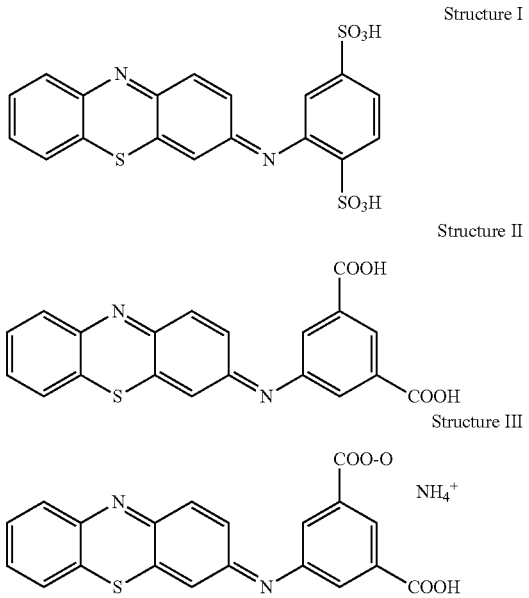

Two electron mediators may have redox potentials that are at least 100 mV lower, more preferably at least 150 mV lower, than ferricyanide. Other two electron mediators may be used.

Electrochemical biosensor systems typically include a measurement device having electrical contacts that connect with electrical conductors in the sensor strip. The sensor strip may be adapted for use outside, in contact with, inside, or partially inside a living organism. When used outside a living organism, a sample of the biological fluid may be introduced to a sample reservoir of the sensor strip. The sensor strip may be placed in the measurement device before, after, or during the introduction of the sample for analysis. When in contact with the living organism, the sensor strip may be attached to the skin where fluid communication is established between the organism and the strip. When inside or partially inside a living organism, the sensor strip may be continually immersed in the fluid or the fluid may be intermittently introduced to the strip for analysis. The sensor strip may include a reservoir that partially isolates a volume of the fluid or be open to the fluid. When in contact with, partially inside, or inside a living organism, the measurement device may communicate with the sensor strip using wires or wirelessly, such as by RF, light-based, magnetic, or other communication techniques.

The conductors of the sensor strip may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

The measurement device applies an input signal to the electrical conductors of the sensor strip. The electrical conductors convey the input signal through the electrodes into the sample. The redox reaction of the measurable species generates an electrical output signal in response to the input signal. The electrical output signal from the strip may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the biological fluid. The processing capability may be in communication with the measurement device, but separate. Communication may be established using wires or wirelessly, such as by RF, light-based, magnetic, or other communication.

In coulometry, the analyte concentration is quantified by exhaustively oxidizing the analyte within a small volume and integrating the current over the time of oxidation to produce the electrical charge representing the analyte concentration. Thus, coulometry captures the total amount of analyte within the sensor strip. An important aspect of coulometry is that towards the end of the integration curve of charge vs. time, the rate at which the charge changes with time becomes substantially constant to yield a steady-state condition. This steady-state portion of the coulometric curve forms a relatively flat current region, thus allowing determination of the corresponding current. However, the coulometric method requires the complete conversion of the entire volume of analyte to reach the steady-state condition unless the true steady-state current is estimated from non-steady-state output. As a result, this method may be time consuming or less accurate due to the estimation. The sample volume of the sensor strip also must be controlled to provide accurate results, which can be difficult with a mass produced device.

Another electrochemical method which has been used to quantify analytes in biological fluids is amperometry. In amperometry, current is measured at a substantially constant potential (voltage) as a function of time as a substantially constant potential is applied across the working and counter electrodes of the sensor strip. The measured output current is used to quantify the analyte in the sample. Amperometry measures the rate at which the electrochemically active species, such as the analyte or mediator, is being oxidized or reduced near the working electrode. Many variations of the amperometric method for biosensors have been described, for example in U.S. Pat. Nos. 5,620,579; 5,653,863; 6,153,069; and 6,413,411.

Voltammetry is another electrochemical method that may be used to quantify analytes in biological fluids. Voltammetry differs from amperometry in that the potential of the input signal applied across the working and counter electrodes of the strip changes continuously with time. The current is measured as a function of the change in potential of the input signal and/or time. Additional information about voltammetry may be found in "Electrochemical Methods: Fundamentals and Applications" by A. J. Bard and L. R. Faulkner, 1980.

Multiple methods of applying the input signal to the strip, commonly referred to as pulse methods, sequences, or cycles, have been used to address inaccuracies in the determined analyte concentration. For example, in U.S. Pat. No. 4,897,162 the input signal includes a continuous application of rising and falling voltage potentials that are commingled to give a triangular-shaped wave. Furthermore, WO 2004/

053476 and U.S. Patent Docs. 2003/0178322 and 2003/0113933 describe input signals that include the continuous application of rising and falling voltage potentials that also change polarity.

Electrochemical decays may be correlated with the analyte concentration in the sample by expressing the decay with an equation describing a line relating current with time by the natural log function (In), for example. Thus, the output current may be expressed as a function of time with an exponential coefficient, where negative exponential coefficients indicate a decay process. After the initial decrease in current output, the rate of decrease may remain relatively constant, thus becoming steady-state, or continue to fluctuate.

The measurement performance of a biosensor system is defined in terms of accuracy and/or precision. Increases in accuracy and/or precision provide for an increase in measurement performance for the biosensor system. Accuracy may be expressed in terms of bias of the sensor's analyte reading in comparison to a reference analyte reading, with larger bias values representing less accuracy, while precision may be expressed in terms of the spread or variance among multiple analyte readings in relation to a mean. Bias is the difference between a value determined from the biosensor and the accepted reference value and may be expressed in terms of "absolute bias" or "relative bias". Absolute bias may be expressed in the units of the measurement, such as mg/dL, while relative bias may be expressed as a percentage of the absolute bias value over the reference value. Reference values may be obtained with a reference instrument, such as the YSI 2300 STAT PLUS™ available from YSI Inc., Yellow Springs, Ohio.

Many biosensor systems include one or more methods to correct the error, and thus the bias, associated with an analysis. The concentration values obtained from an analysis with an error may be inaccurate. The ability to correct these inaccurate analyses may increase the accuracy and/or precision of the concentration values obtained. An error correction system may compensate for one or more errors, such as error arising when the measurable species concentration does not correlate with the analyte concentration. For example, when a biosensor system determines the concentration of a reduced mediator generated in response to the oxidation of an analyte, any reduced mediator not generated by oxidation of the analyte will lead to the system indicating that more analyte is present in the sample than is correct due to mediator background. Thus, "mediator background" is the bias introduced into the measured analyte concentration attributable to measurable species not responsive to the underlying analyte concentration.

Measurement inaccuracies also may arise when the output signal does not correlate to the measurable species concentration of the sample. For example, when a biosensor system determines the concentration of a measurable species from output signal currents, output currents not responsive to the measurable species will lead to the system indicating that more analyte is present in the sample than is correct due to interferent current. Thus, "interferent bias" is the bias introduced into the measured analyte concentration attributable to interferents producing output currents not responsive to the underlying analyte concentration.

As may be seen from the above description, there is an ongoing need for electrochemical sensor systems having improved measurement performance, especially those that may provide an increasingly accurate and/or precise determination of a biological analyte concentration. The systems, devices, and methods of the present invention overcome at least one of the disadvantages associated with conventional systems.

SUMMARY

A method for measuring at least one analyte in a sample includes applying to the sample an input signal having a first duty cycle including an amperometric excitation and a first relaxation and a second duty cycle including a voltammetric excitation and a second relaxation or a first duty cycle including a voltammetric excitation and a first relaxation and a second duty cycle including an acyclic scan and a second relaxation. An output signal is detected that includes output currents responsive to the amperometric and voltammetric excitations. A portion of the output signal is correlated with the concentration of the at least one analyte in the sample.

A measurement device for determining the concentration of an analyte in a sample includes a signal interface including at least two contacts, and electrical circuitry establishing electrical communication between the at least two contacts and a signal generator. The electrical circuitry includes a processor in electrical communication with the signal generator and a storage medium. The processor is operable to apply an input signal from the signal generator to the at least two contacts. The input signal may include a first duty cycle having an amperometric excitation and a first relaxation and a second duty cycle having a voltammetric excitation and a second relaxation. The input signal may include a first duty cycle having a voltammetric excitation and a first relaxation and a second duty cycle having an acyclic san and a second relaxation. The processor is operable to detect an output signal at the at least two contacts. The output signal may include output currents responsive to the amperometric excitation, the voltammetric excitation, and/or the acyclic scan. The processor is operable to correlate a portion of the output signal into a concentration of at least one analyte in the sample.

A method for identifying an ionizable species in a sample includes applying an input signal including an acyclic scan to the sample, where the acyclic scan includes a forward excitation and a reverse excitation. Detecting an output signal, the output signal including output currents responsive to the acyclic scan and identifying the ionizable species from the output currents responsive to the forward excitation of the acyclic scan. The method may include identifying the ionizable species from a first ratio and a second ratio of the output currents when the second ratio is less than 1. The first ratio may be determined from an initial output current responsive to the forward excitation of the acyclic scan and a midpoint output current responsive to the forward excitation of the acyclic scan. The second ratio may be determined from the midpoint output current responsive to the forward excitation of the acyclic scan and a final output current responsive to the forward excitation of the acyclic scan.

Other systems, methods, features, and advantages of the invention will be, or will become, apparent to one with skill in the art upon examination of the following figures and detailed description. It is intended that all such additional systems, methods, features and advantages be included within this description, be within the scope of the invention, and be protected by the claims that follow.

BRIEF DESCRIPTION OF THE DRAWINGS

The invention may be better understood with reference to the following drawings and description. The components in the figures are not necessarily to scale, emphasis instead being placed upon illustrating the principles of the invention.

DETAILED DESCRIPTION

Figure 1:
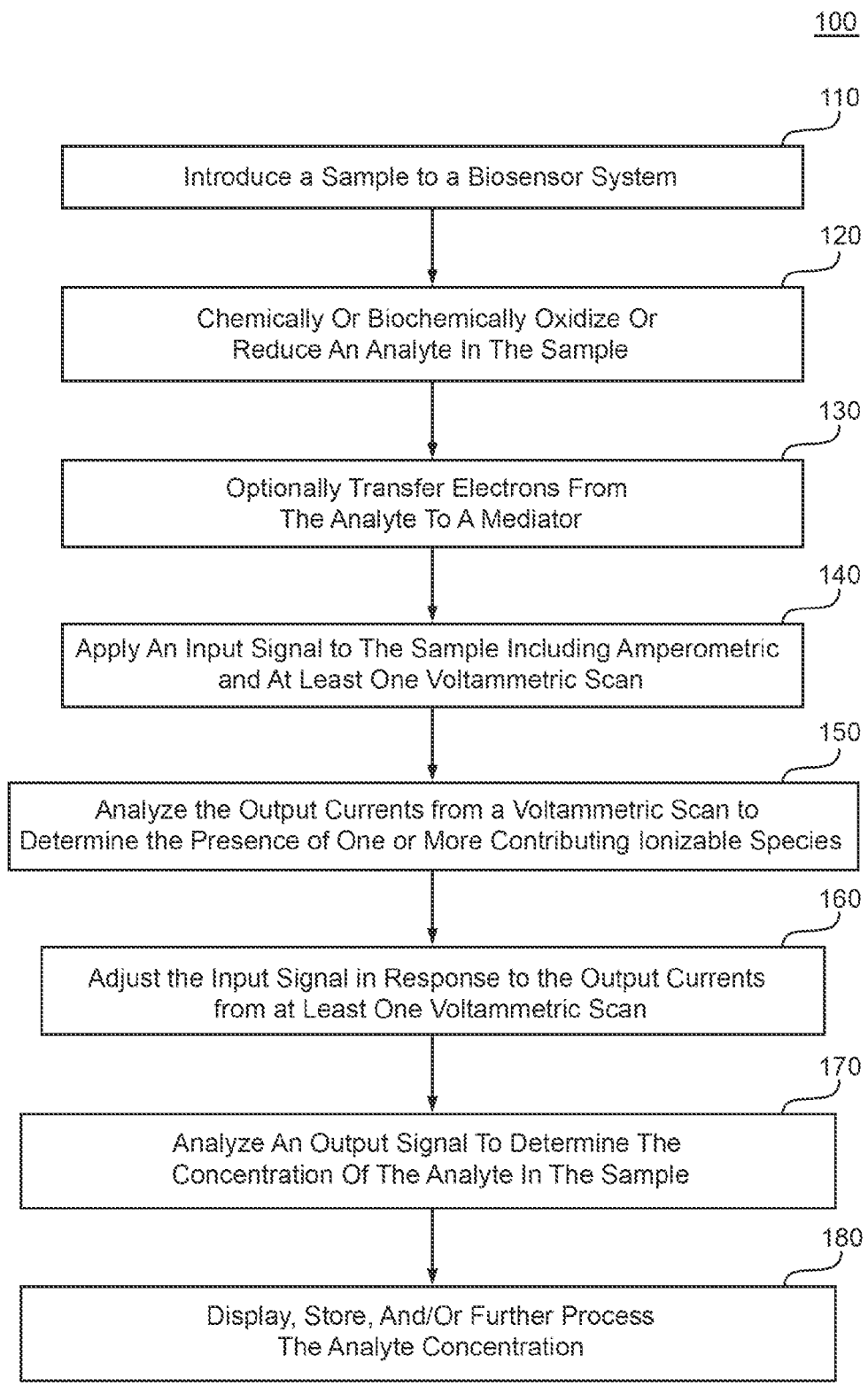
FIG. 1 represents an electrochemical analytic method for determining the presence and/or concentration of an analyte in a sample where the input signal is adjusted in response to the output currents from a voltammetric scan.

An electrochemical analytic sensor system determines the concentration of an analyte in a sample, such as the glucose concentration of whole blood. The system includes a device that applies an input signal including amperometric and at least one voltammetric duty cycle to the sample. The input signal may lack an amperometric duty cycle when at least one acyclic scan duty cycle is applied to the sample. Each duty cycle includes an excitation and a relaxation. Excitations may be amperometric or voltammetric. The system adjusts amperometric and/or voltammetric portions of the input signal in response to output currents obtained from voltammetric portions of the input signal. The system may adjust the input signal to reduce output currents responsive to interferents while reducing output current non-linearity, thus, increasing measurement performance.

The system may identify the presence and/or identity of one or more ionizable species in the sample in response to output currents obtained from one or more voltammetric scans. The system may identify the presence and/or identity of one or more ionizable species in the sample in response to output currents obtained from one or more linear scans. The system may identify the presence and/or identity of one or more ionizable species in the sample in response to output currents obtained from the forward excitation of one or more acyclic scans. The system may use derivatives and/or ratios or other methods to determine the presence and/or oxidation potential of one or more ionizable species in the sample from output currents responsive to voltammetric scans. The system may select an amperometric excitation and/or acyclic scan potential based on ratios determined from current values obtained from acyclic scans.

By adjusting the potential of one or more amperometric excitations and/or one or more acyclic scans in response to output currents obtained from voltammetric scans, the output currents responsive to one or more interferents may be reduced. The output currents obtained from the voltammetric scans also may be used to adjust the potential of one or more amperometric excitations and/or one or more acyclic scans to reduce the non-linearity of the output currents responsive to one or more ionizable species. In relation to a conventional system that operates at a single, relatively high potential to reduce the possibility of non-linear response, the system may adjust the potential of one or more excitations to reduce non-linearity of the output currents while reducing output currents responsive to interferents.

The output currents obtained from the voltammetric scans also may be used to adjust the potential of one or more amperometric excitations and/or one or more acyclic scans to determine analyte concentration and further adjusted to determine interferent concentration. Thus, by adjusting the potential of the input signal the system can determine the concentration of one or more ionizable species in the sample and report or use the determined values to correct reported concentration values. By adjusting the scan rate of one or more linear or acyclic scans in response to output currents obtained from linear or acyclic scans, the redox potentials of two or more ionizable species may be better defined.

The system may compare the output currents from one or more amperometric excitations to determine the concentration of analytes, interferents, or other ionizable species in the sample. The system may determine the analyte, interferent, or other ionizable species concentration of the sample from output currents obtained from one or more acyclic scans. The system may average the output currents from an acyclic scan to determine the analyte, interferent, or other ionizable species concentration of the sample. The system may apply one or more data treatments, including those based on semi-integration, derivatives, and semi-derivatives to analyze the data.

Amperometric duty cycles advantageously require simpler electronics and methods to implement, but may provide very short transient decays with short pulse widths. For example, averaging current values recorded during the decay from a short pulse width amperometric input signal may decrease the measurement performance of the system because of variability in the output currents. In contrast, voltammetric scans, either linear or acyclic may provide output currents in a finite potential range that are relatively constant. The relative constancy of the voltammetric output signals may be improved when the voltammetric input signal is within the diffusion-limited current (DLC) region of the measurable species being excited. As the constancy of the current values improve, the measurements become easier and data manipulation techniques, such as signal averaging, may provide increases in the measurement performance of the system.

FIG. 1 represents an electrochemical analysis 100 for determining the presence and/or concentration of an analyte in a sample. In sample introduction 110, the sample is introduced to the biosensor. In redox reaction 120, a portion of the analyte in the sample undergoes a redox reaction. In electron transfer 130, electrons are optionally transferred from the analyte to a mediator. In this manner, the concentration of ionized mediator in the sample becomes responsive to the concentration of the analyte in the sample. In input signal application 140, an input signal including amperometric and voltammetric duty cycles is applied to the sample. In voltammetric output current analysis 150, output currents responsive to at least one voltammetric scan are analyzed to determine the presence and/or identity of one or more contributing ionizable species. In input signal adjustment 160, the input signal is adjusted in response to the output currents from the at least one voltammetric scan. In sample determination 170, the presence and/or concentration of one or more contributing ionizable species in the sample, such as the analyte, is determined from one or more output signals. In sample concentration transmission 180, the determined ionizable species concentration may be displayed, stored, further processed, and the like.

In the sample introduction 110, the sample is introduced to the sensor portion of the system, such as a sensor strip. The sensor strip includes at least one working and at least one counter electrode. The electrodes may include one or more reagent layers. The working electrode may include a diffusion barrier layer that is integral to a reagent layer or that is distinct from the reagent layer. The diffusion barrier layer provides a porous space having an internal volume where a measurable species may reside. A more detailed description of the implementation and use of diffusion barrier layers may be found in U.S. Patent Doc. 2007/0246357, entitled "Concentration Determination in a Diffusion Barrier Layer."

In the redox reaction 120 of FIG. 1, a portion of the analyte present in the sample is chemically or biochemically oxidized or reduced, such as by an oxidoreductase. This occurs as the sample hydrates the reagents. Upon oxidation or reduction, electrons optionally may be transferred between the analyte and a mediator in the electron transfer 130. Thus, an ionized measurable species is formed, such as from the analyte or a mediator. It may be beneficial to provide an initial time delay, or "incubation period," for the reagents to react with the analyte.

In the input signal application 140 of FIG. 1, an input signal is applied to the sample. Input signals are electrical signals, such as current or potential, that change significantly in amplitude or turn on and off at a set sequence. Thus, the input signal is a sequence of excitations separated by relaxations. The system may apply one or more input signals to the sample, including those used to determine the presence and/or concentration of the analyte and those used to determine other factors, such as the hematocrit content of the sample or the interferent currents.

Input signals include multiple duty cycles and may have one or more pulse interval. A pulse interval is the sum of the pulse or excitation width and the relaxation width constituting a duty cycle. Each pulse has an amplitude and a width. The amplitude indicates the intensity of the potential, the current, or the like of the excitation signal. The amplitude may be substantially constant, such as during an amperometric excitation, or vary, such as during a voltammetric scan. The pulse width is the time duration of the amperometric excitation or voltammetric scan. The pulse widths of an input signal may vary or be essentially the same. Each relaxation has a relaxation width, which is the time duration of the relaxation. The relaxation widths of an input signal may vary or be substantially the same.

By adjusting the pulse and relaxation widths of the duty cycles, gated input signals may improve the measurement performance of the system. While not wishing to be bound by any particular theory, this improvement in measurement performance may result from drawing the measurable species excited at the working electrode from the interior of a diffusion barrier layer.

Preferable input signals include at least 3, 4, 6, 8, or 10 duty cycles applied during less than 30, 10, or 5 seconds. More preferably, at least 3 duty cycles are applied within 10 seconds. Input signals including at least 4 duty cycles applied in less than 7 seconds are especially preferred at present. Preferably, the width of each excitation pulse is independently selected from between 0.1 and 3 seconds and more preferably from between 0.2 and 1.2 second. At present, especially preferred input signal pulse widths are independently selected from between 0.3 and 0.8 seconds. Preferable pulse intervals are in the range of less than 3, 2.5, or 1.5 seconds. At present, input signals having pulse widths of 0.3 to 0.5 second and pulse intervals from 0.7 to 2 seconds are especially preferred. The input signal may have other pulse widths and intervals.

The repetitive excitation-relaxation nature of the duty cycles directly contrast with conventional methods where voltage is continuously applied to and current is continuously drawn from the sensor strip. For these conventional methods, the applied voltage may have a fixed potential or may have a potential that is swept from a positive to a negative potential or from a positive or a negative potential to a zero potential relative to a reference potential. Even at a zero relative potential, these methods continuously draw current from the sensor strip during the read pulse, which permits the electrochemical reaction to continue throughout the read pulse. Thus, in these conventional methods the reaction that produces measurable species responsive to the analyte concentration and the diffusion of the measurable species to the working electrode are both affected by current during the zero potential portion of the read pulse. The input signals of the analysis 100 are markedly different from conventional methods that use a single long duration pulse with multiple measurements, such as those disclosed in U.S. Pat. No. 5,243,516.

Each amperometric duty cycle includes an excitation during which currents (amperage) may be measured from a sensor strip while a potential (voltage) applied to the sensor strip is maintained substantially constant with time. The potential of the amperometric excitation may be maintained within $\pm 10\%$, $\pm 5\%$, or $\pm 2\%$ with time, preferably within $\pm 2\%$ with time. Each voltammetric duty cycle includes a linear, cyclic, or acyclic scan during which currents (amperage) may be measured from the sensor strip while a potential (voltage) applied to the strip is varied substantially linearly with time. The potential may be maintained within $\pm 10\%$, $\pm 5\%$, or $\pm 2\%$ of linearity with time, preferably within $\pm 2\%$ of linearity with time. The potential may be varied continuously with time during the voltammetric scan. The input signal application 140 may include an amperometric and at least one voltammetric duty cycle. The input signal application 140 may lack an amperometric duty cycle when at least one acyclic scan duty cycle is applied to the sample.

In voltammetric output current analysis 150, output currents responsive to at least one voltammetric scan are analyzed to determine the presence and/or identity of one or more ionized species. More than one voltammetric scan may be used, and more than one type of voltammetric scan may be used. The presence and/or identity of one or more ionizable species in the sample may be identified in response to output currents obtained from a linear scan, a cyclic scan, and/or the forward excitation of one or more acyclic scans. The ionized species may be one or more measurable species correlated with one or more analytes in the sample or ionized interferents and the like. Derivatives, ratios, or other methods may be used to determine the presence of one or more ionizable species in the sample from output currents responsive to the voltammetric scans.

In input signal adjustment 160, the input signal is adjusted in response to the output currents from the at least one voltammetric scan. Amperometric excitations or voltammetric scans may be adjusted in response to the output currents from the at least one voltammetric scan. The adjustments may be made to reduce or eliminate interferent currents from the output currents obtained from amperometric excitations or acyclic scans. The adjustment may be made to reduce or eliminate non-linear response from output currents obtained from amperometric excitations or acyclic scans. The adjustment may be made to determine the concentration of one ionizable species instead of another. One or more adjustments may be made to the input signal to address one or more of these concerns. Thus, the system may operate at multiple potentials responsive to the ionizable species of a specific sample.

In sample determination 170, output signals responsive to the input signal are analyzed to determine the presence and/or concentration of one or more ionizable species in the sample. The output signals may include currents measured during all or part of the amperometric excitations and/or voltammetric scans. The output signals also may or may not include currents measured during a relaxation or part of a relaxation. The output signals also may include currents and/or potentials monitored at the working electrode during at least a portion of the relaxation, which are not used in determining the concentration of the analyte in the sample. As more than one ionizable species in the sample may be ionized by different portions of the input signal, the presence, and/or concentration of multiple analytes, mediators, interferents, and the like may be determined. Additional current, time, and/or other values also may be analyzed. While the sample determination 170 follows the voltammetric output current analysis 150 and the input signal adjustment 160 in FIG. 1, this is not required. One or more ionizable species concentrations could be determined and then modified with information obtained after the input signal adjustment 160.

A more in-depth discussion of data treatments for transforming electrochemical currents and the related digital implementations may be found in Bard, A. J., Faulkner, L. R., "Electrochemical Methods: Fundamentals and Applications," 1980; Oldham, K. B.; "A Signal-Independent Electroanalytical Method," *Anal. Chem.* 1972, 44, 196; Goto, M., Oldham, K. B., "Semi-integral Electroanalysis: Shapes of Neopolarograms," *Anal. Chem.* 1973, 45, 2043; Dalrymple-Alford, P., Goto, M., Oldham, K. B., "Peak Shapes in Semi-differential Electroanalysis," *Anal. Chem.* 1977, 49, 1390; Oldham, K. B., "Convolution: A General Electrochemical Procedure Implemented by a Universal Algorithm," *Anal. Chem.* 1986, 58, 2296; Pedrosa, J. M., Martin, M. T., Ruiz, J. J., Camacho, L., "Application of the Cyclic Semi-Integral Voltammetry and Cyclic Semi-Differential Voltammetry to the Determination of the Reduction Mechanism of a Ni-Porphyrin," *J. Electroanal. Chem.* 2002, 523, 160; Klicka, R, "Adsorption in Semi-Differential Voltammetry," *J. Electroanal. Chem.* 1998, 455, 253.

In sample concentration transmission 160, a measurement device may display, transmit by wire or wirelessly, store for future reference, further process, and/or use one or more of the determined ionizable species concentrations for additional calculations. For example, the value determined for one analyte, mediator, or interferent may be modified with the value determined for another analyte, mediator, or interferent to increase the measurement performance of the system.

Figure 2:
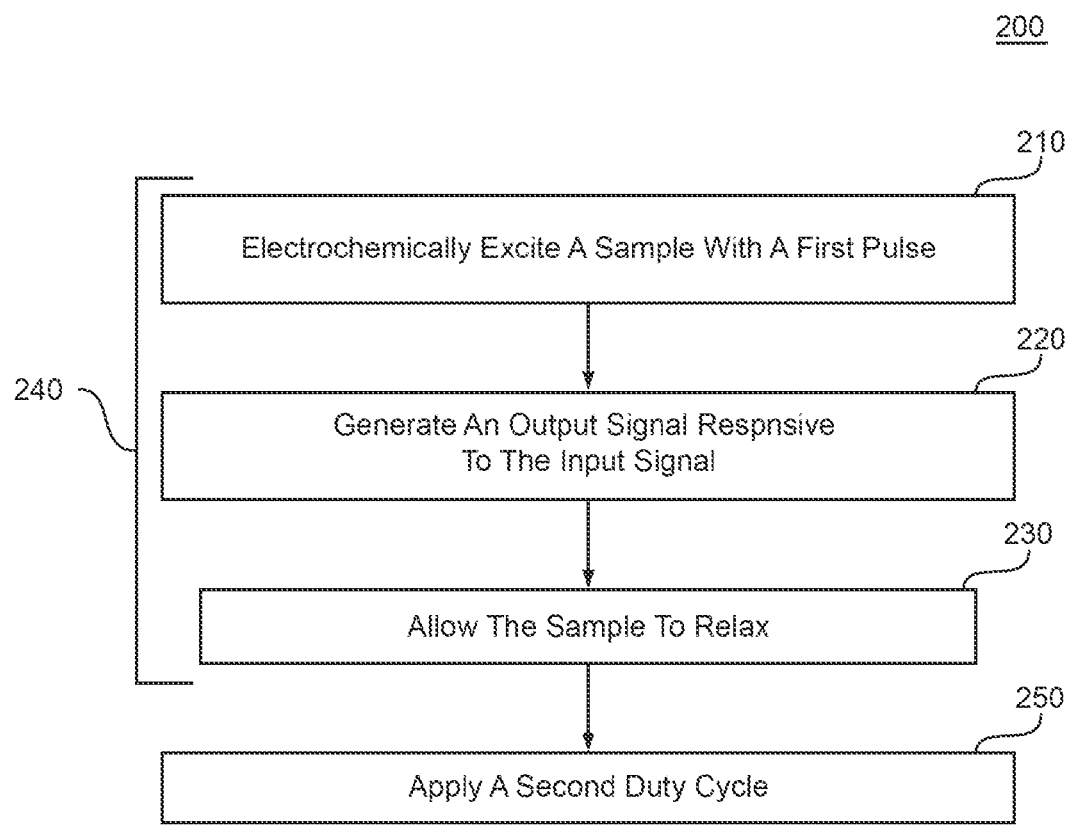
FIG. 2 represents the application of an input signal.

FIG. 2 represents an input signal 200, as could be applied in 140 of FIG. 1. In first pulse 210, the sample is electrochemically excited with the first pulse of the input signal. In output signal generation 220, an output signal is generated in response to the input signal. In relaxation 230, the sample is allowed to relax. In combination, the pulse 210, the output signal generation 220, and the relaxation 230 constitute a duty cycle 240. In second duty cycle 250, the duty cycle 240 is repeated with a second pulse replacing the first pulse 210 of the input signal 200.

In the first pulse 210 of FIG. 2, the system ionizes a ionizable species. The pulse may be amperometric, thus having a substantially constant voltage and polarity throughout its duration. Thus, amperometry may determine the concentration of an analyte in a sample by electrochemically measuring the oxidation or reduction rate of a ionizable species at a substantially constant potential. Conversely, the pulse may be voltammetric, thus having a potential that is changed or "scanned" in a substantially linear manner through multiple voltages at a substantially constant polarity. In this manner, voltammetry may determine the concentration of an analyte in a sample by measuring the oxidation or reduction rate of the ionizable species at a potential varying with respect to time.

In the output signal generation 220 of FIG. 2, the system generates an output signal in response to one or more ionizable species in the sample and the first pulse 210 of the input signal. The output signal, such as one or more current values, may be measured continuously or intermittently and may be recorded as a function of time. Output signals may include those that decline initially, those that increase and then decline, those that reach a steady-state, and those that are transient. Steady-state currents are observed when the current change with respect to time is substantially constant. Instead of conventional steady-state or slowly decaying currents, transient (rapidly decaying) current values may be obtained from input signals having multiple duty cycles.

In the relaxation 230, the sample undergoes relaxation. During the relaxation 230, the current is reduced to at least one-half the current flow at the excitation maxima or by at least an order of magnitude in relation to the current flow at the excitation maxima. During the relaxation 230 the current flow may be reduced to a zero current state, which may be provided by opening the circuit through the sensor strip or other means. The electrical circuit may be closed to provide an excitation (on state) or opened to provide a relaxation (off state) mechanically, electrically, or by other methods. A zero current state does not include time periods when an electrical signal is present, but has essentially no amplitude.

During the relaxation 230, an ionizing agent, such as an oxidoreductase, may react with an analyte to generate additional measurable species without the effects of an electric potential. For example, a glucose biosensor including glucose oxidase and a ferricyanide mediator as reagents will produce additional ferrocyanide (reduced mediator) responsive to the analyte concentration of the sample without interference from an electric potential during the relaxation 230.

During the second duty cycle 250 of FIG. 2, the first pulse 210 is replaced with a second pulse, which in combination with the relaxation 230, provides the second duty cycle 250 of the input signal. The second duty cycle 250 may have the same or different pulse widths and/or intervals as the first duty cycle 240. The second pulse may be amperometric or voltammetric. As for the first pulse 210, the second pulse excites an ionizable species, which may be an ionized analyte, mediator, or interferent, for example.

While the first and second pulses may be amperometric or voltammetric, they are different. Thus, if the first pulse 210 is amperometric, the second pulse is voltammetric; and if the first pulse 210 is voltammetric, the second pulse is amperometric. One or more amperometric, voltammetric, or other pulse may precede the first pulse 210, separate the first pulse 210 from the second pulse, and/or follow the second pulse. Other combinations of amperometric excitations and voltammetric scans may be used.

Figure 3A:
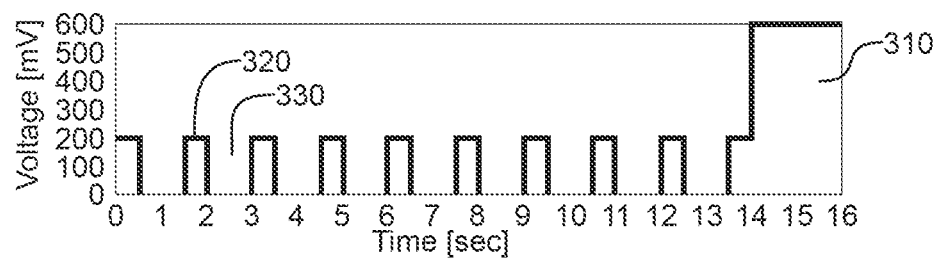
FIGS. 3A-3D represent gated amperometric input signals where multiple duty cycles were applied to the sensor strip after introduction of the sample.
Figure 3B:
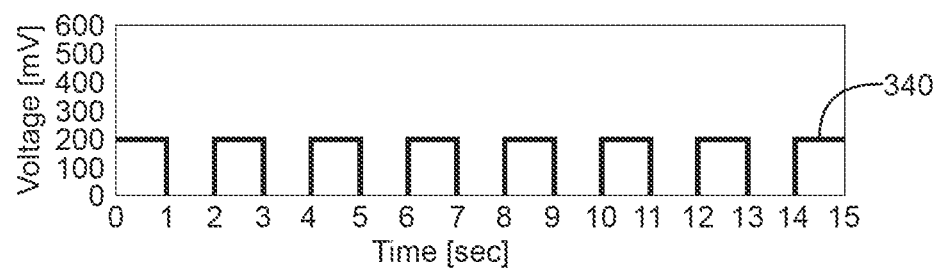
Figure 3C:
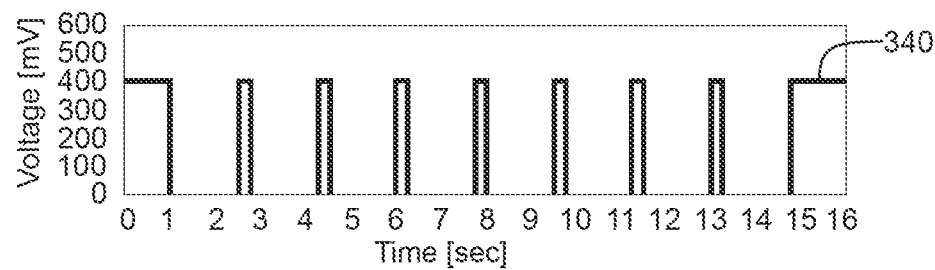

FIGS. 3A-3D represent gated amperometric input signals where multiple duty cycles were applied to the sensor strip after introduction of the sample. In these representations, square-wave pulses were used; however, other wave types compatible with the sensor system and test sample also may be used. For example, each of the depicted excitations could include multiple shorter duration pulses. FIG. 3A depicts a 9 duty cycle input signal where 0.5 second pulses are separated by 1 second open circuit delays to give a redox intensity (RI) of 0.357 (5/14), where RI is the total excitation time divided by the sum of the total excitation time and the total relaxation time delays for an input signal. Thus, in FIG. 3A, the second duty cycle has an excitation 320 and a relaxation 330. The output signals generated from gated amperometric input signals may be expressed as currents recorded as a function of time.

The input signal of FIG. 3A also includes a terminal read pulse 310 of longer duration that includes an increased voltage. The increased voltage of this terminal read pulse provides the ability to detect species having a higher oxidation potential, such as control solutions. Terminal read pulses having substantially the same voltage as the excitation pulses of the duty cycles, such as terminal read pulse 340 of FIG. 3B also may be used. A more complete discussion regarding terminal read pulses may be found in U.S. Patent Doc. 2009/0014339, entitled "Oxidizable Species as an Internal Reference in Control Solutions for Biosensors."

Figure 3D:
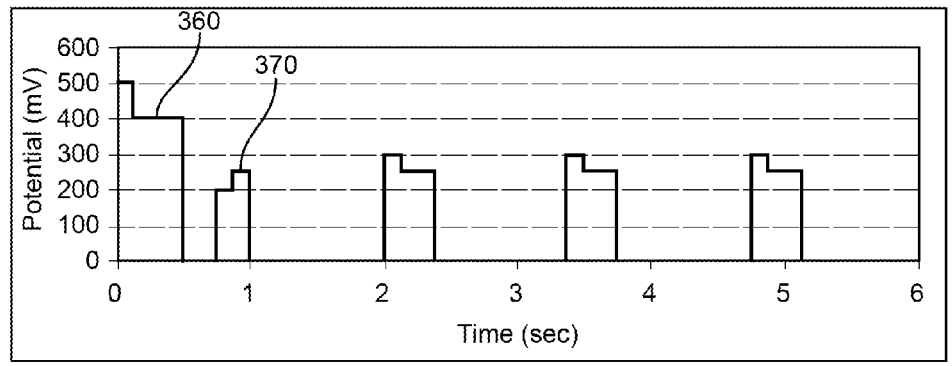

FIG. 3D represents a gated amperometric input signal where an initial pulse 360 is applied at a higher voltage than the following four pulses. In addition, the relaxation widths are varied between the initial pulse 360 and the second pulse 370, when compared with the relaxation widths of the remaining pulses. In contract to the amperometric excitations of FIGS. 3A-3C, the amperometric excitations of FIG. 3D each include two portions of a substantially constant voltage to provide a stepped-amperometric pulse. Thus, gated amperometric input signals having more than one substantially constant voltage per pulse may be used.

Figure 4A:
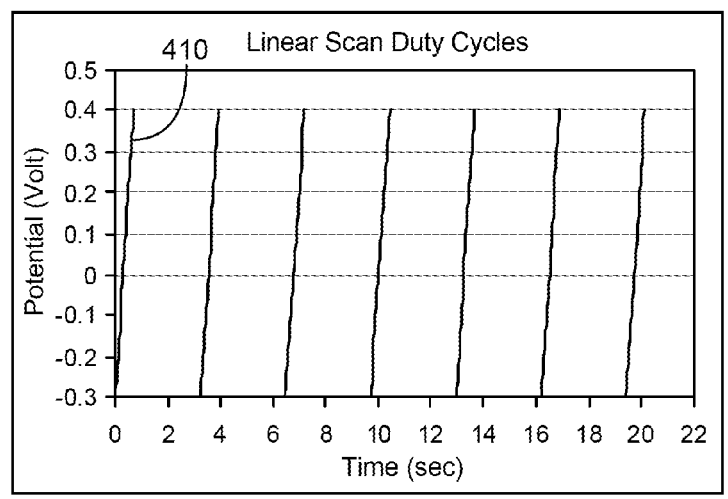
FIGS. 4A-4D represent gated voltammetric input signals where the potential is varied with time.
Figure 4B:
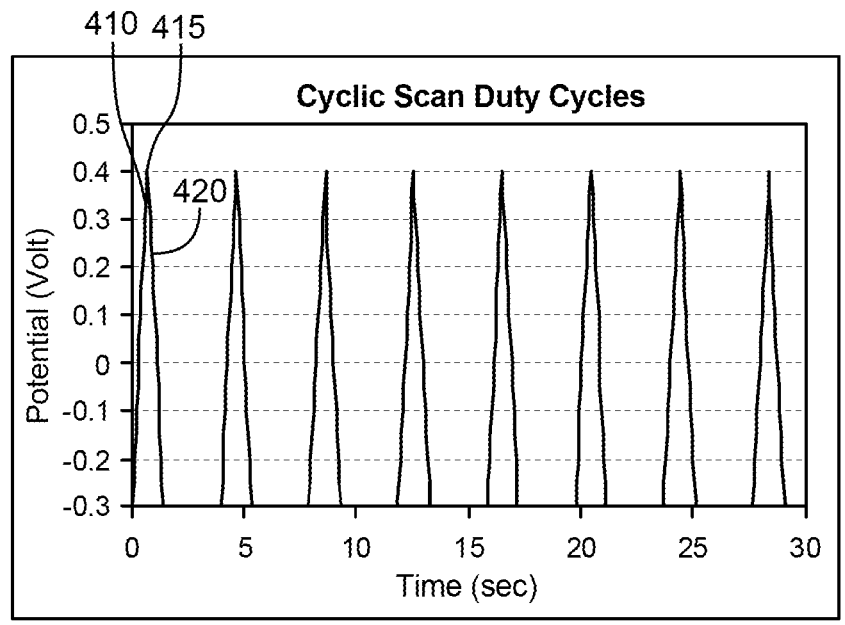
Figure 4C:
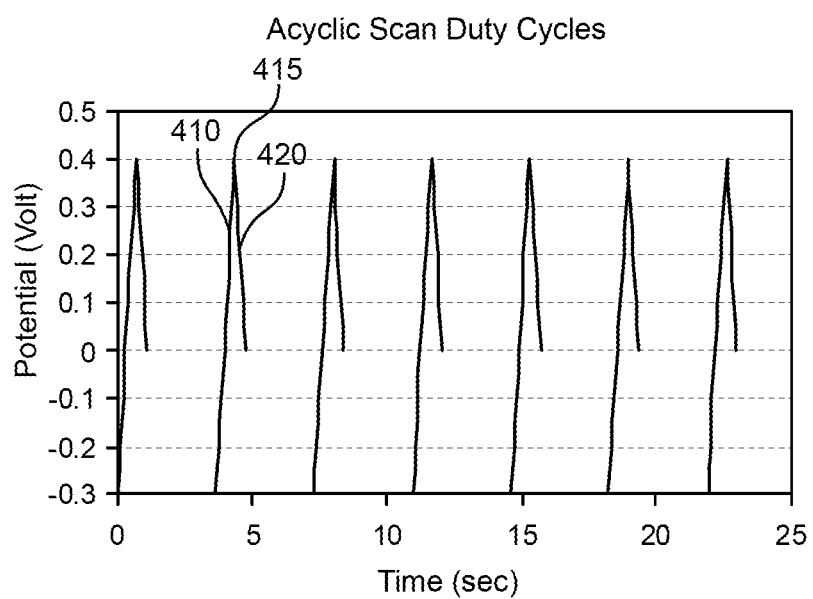
Figure 4D:
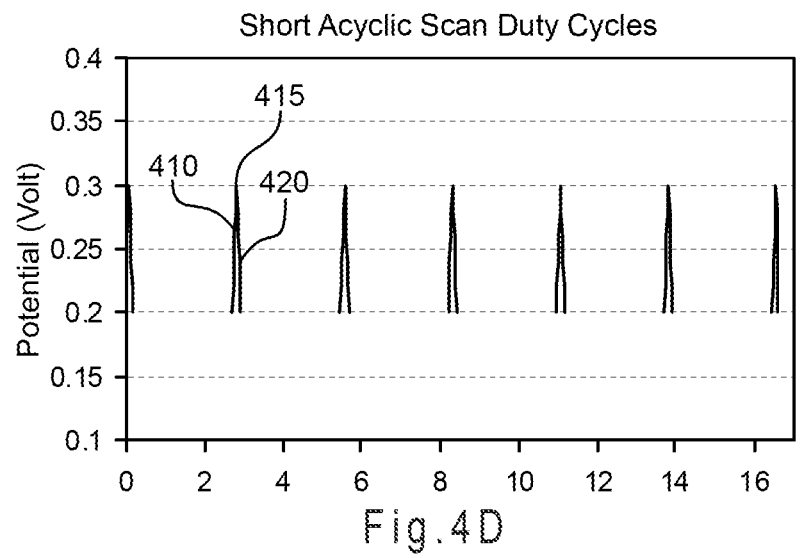

In contrast to the amperometric excitations of FIGS. 3A-3D, FIGS. 4A-4F represent gated voltammetric duty cycles where the potential is varied with time. FIG. 4A represents gated linear scans including a forward scan 410, while FIG. 4B represents gated cyclic scans including the forward scan 410 coupled with a reversing-point 415 and a reverse scan 420. A reversing-point is the point in a cyclic or acyclic scan when the forward scan is stopped and the reverse scan begins. In combination, the forward scan 410 and the reverse scan 420 may substantially cover the potential range of a mediator, such as ferricyanide. FIGS. 4C and 4D represent gated acyclic scans, where in FIG. 4C the forward scan starts at a different voltage than where the reverse scan stops and in FIG. 4D the forward and reverse scans substantially occur in the DLC region of one species of a redox couple, such as under the ferrocyanide species of the ferricyanide/ferrocyanide redox couple.

Figure 4E:
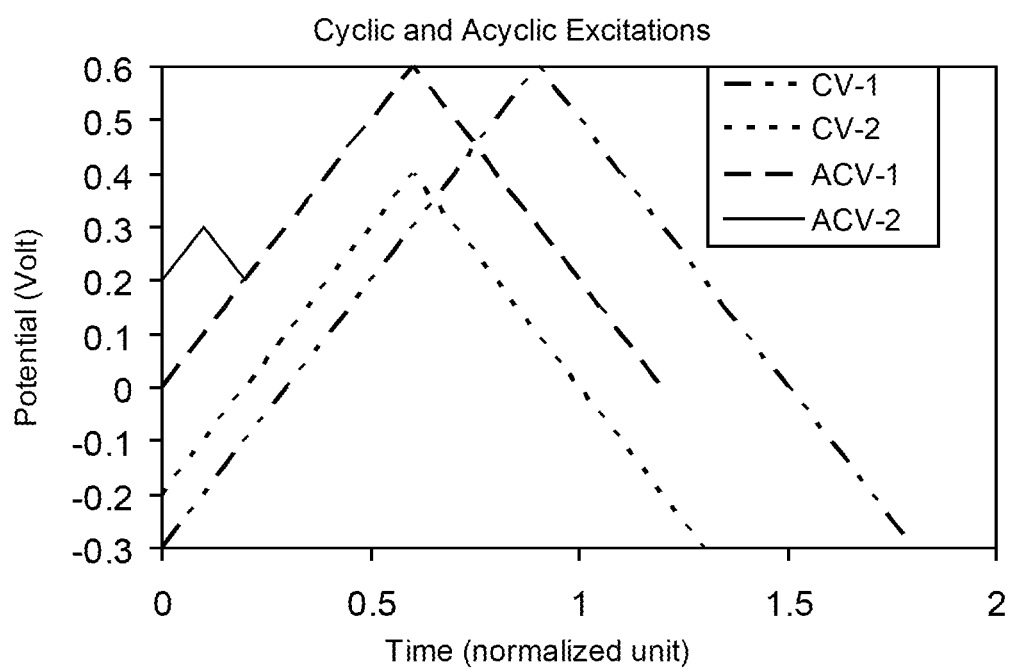
FIG. 4E compares cyclic and acyclic scans.

FIG. 4E compares cyclic and acyclic scans. Cyclic scan CV-1 starts at an initial potential of −0.3 V, where the reduced species of the redox couple is dominant, increases to a +0.6 V reversing point potential, and returns to the initial −0.3 V potential. Cyclic scan CV-2 starts at an initial potential of −0.2 V, where the reduced species of the redox couple is dominant, increases to a +0.4 V reversing point potential, and returns to the initial −0.2 V potential.

Acyclic scan ACV-1 starts at an initial potential of 0 V, where the reduced and oxidized species of the redox couple have similar concentrations, increases to a +0.6 V reversing point potential, and returns to the initial 0 V potential. Acyclic scan ACV-2 starts at an initial potential of +0.2 V, increases to a +0.3 V reversing point potential, and returns to the initial +0.2 V potential. Preferably, the +0.2 V and +0.3 V potentials are within the DLC region of the redox couple. For example, and as determined from cyclic scan CV-1, ferrocyanide has a plateau region from approximately from +0.1 V to +0.6 V when compared against the redox potential of the ferricyanide/ferrocyanide redox couple. Other starting, reversing, and ending potentials may be used, depending on multiple factors, such as the redox profile of the redox couple.

Figure 4F:
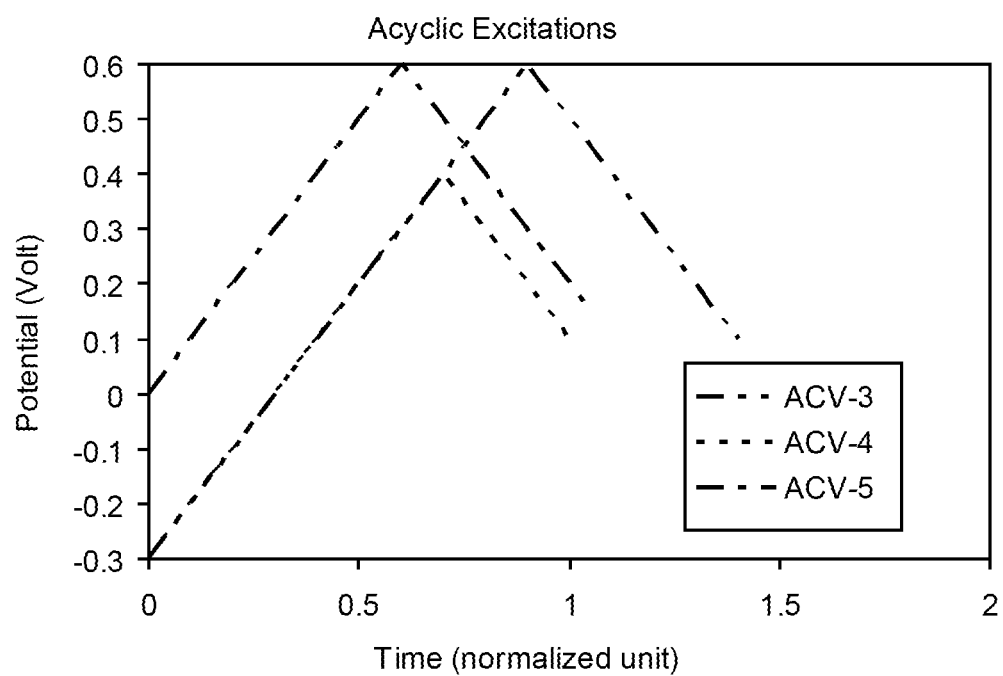
FIG. 4F represents additional acyclic scans having different starting, reversing, and ending potentials.

FIG. 4F represents additional acyclic scans having different starting, reversing, and ending potentials. Acyclic scan ACV-3 starts at an initial potential of −0.3 V, where the reduced species of the redox couple is dominant, increases to a +0.6 V reversing point potential, and returns to a +0.1 V potential before the reverse potential scan substantially initiates reduction of the redox couple. Acyclic scan ACV-4 starts at an initial potential of −0.3 V, where the reduced species of the redox couple is dominant, increases to a +0.4 V reversing point, and returns to a +0.1 V potential before the reverse potential scan substantially initiates reduction of the redox couple. Acyclic scan ACV-5 starts at an initial potential of 0 V, where the reduced and oxidized species of the redox couple have similar concentrations, increases to a +0.6 V reversing point, and returns to an about +0.15 V potential before the reverse potential scan substantially initiates reduction of the redox couple. Other starting, reversing, and ending potentials may be used, depending on multiple factors, such as the redox profile of the redox couple.

During a linear scan, such as forward scan 410 depicted in FIG. 4A, the current at the working electrode is measured while the potential at the working electrode changes linearly with time at a constant rate. The scan range, such as from −0.5 V to +0.5 V, may cover the reduced and oxidized states of a redox couple so that a transition from a first state to a second state occurs. Redox couples are two conjugate species of a chemical substance having different oxidation numbers where reduction of the species having the higher oxidation number produces the species having the lower oxidation number and oxidation of the species having the lower oxidation number produces the species having the higher oxidation number.

A voltammogram (a plot of current versus voltage) may be characterized by a plot that starts at an initial current, reaches a peak current, and decays to a lower DLC level during the scan. The initial current is substantially dependent on the applied potential, while the DLC is not. If the scan is slow enough, the DLC region may be seen as a plateau region in a voltammogram.

The DLC region is believed to represent a state where the oxidation or reduction of the ionizable species at the conductor surface reaches a maximum rate substantially limited by diffusion. The diffusion may be limited by the rate at which the ionizable species travels from the sample to the conductor surface. Alternatively, when the working electrode of the sensor strip includes a diffusion barrier layer, the diffusion may be limited by the rate at which the ionizable species travels from the diffusion barrier layer to the conductor surface.

After completion of the forward scan 410, for a cyclic or acyclic scan, such as those depicted in FIGS. 4B and 4C-4D, respectively, a reversed potential linear scan 420 is applied. The reversed potential linear scan 420 may be applied at substantially the same rate as the forward scan 410 or at a different rate. Thus, the potential is scanned from a first lower value to a higher value and back to a second lower value, where the first and second lower values may or may not be the same for cyclic or acyclic scans, respectively. Cyclic, and in some instances acyclic, scans may examine the transition of a redox species from a reduced state to an oxidized state (and vice versa) in relation to the applied potential or in relation to the diffusion rate of the redox species to the conductor surface.

In relation to a linear scan, cyclic and acyclic scans may provide a better representation of the DLC region of the scan. Cyclic and acyclic scans also may be especially advantageous for quantifying the DLC from quasi-reversible redox couples at fast scan rates. Quasi-reversible redox couples are redox couples where the separation between the forward and reverse scans of the semi-integral is larger than 30 mV at the half-height of the $si_{ss}$ transition for the redox couple. Additional information about linear and cyclic scan voltammetry may be found in "Electrochemical Methods: Fundamentals and Applications" by A. J. Bard and L. R. Faulkner, 1980.

Poorly activated electrodes may not provide an acceptable DLC condition even with reversible or quasi-reversible redox couples. Thus, electrode activation procedures, such as those described in U.S. Pat. No. 5,429,735, may be used to achieve the preferred electrode activity.

In addition to pulse width, which may be shorter as represented in FIG. 4D or longer as represented in FIG. 4B, the rate (mV/sec) at which the potential is changed (scanned) also may be varied. For gated input signals, voltammetric scans changing at the rate of at least 176 mV/sec are preferred, with scan rates of from 200 to 5000 mV/sec being more preferred, and scan rates of from 500 to 1500 mV/sec being especially preferred at present.

Gated input signals may have varying redox intensities (RI) depending on the pulse and relaxation widths of the duty cycle. The output signals generated from gated input signals may be expressed as currents recorded as a function of time. A more detailed discussion of gated amperometric input signals may be found in U.S. Patent Doc. 2008/0173552, entitled "Gated Amperometry." The output signals generated from gated voltammetric input signals may be expressed as currents recorded as a function of the applied voltage with time. A more detailed discussion of gated voltammetric input signals may be found in U.S. Patent Doc. 2008/0179197, entitled "Gated Voltammetry."

The higher the RI for an input signal, the less mediator background inaccuracy may be introduced into the analysis by the mediator. The input signals represented in FIGS. 3A-3D and 4A-4C are oxidative pulses, designed to excite (e.g. oxidize) a reduced mediator, which is the measurable species. Thus, the greater the oxidative current applied to the sensor strip in a given time period, the less chance that mediator reduced by pathways other than oxidation of the analyte contributes to the recorded current values. In combination, the multiple duty cycles of the gated amperometric and voltammetric input signal may eliminate the need for an initial pulse to renew the oxidation state of the mediator. For ferricyanide and the organic two electron mediators of Structures I-III, input signals may have RI values of at least 0.01, 0.3, 0.6, or 1, with RI values of from 0.1 to 0.8, from 0.2 to 0.7, or from 0.4 to 0.6 being preferred. Other RI values may be used and other RI values may be preferred for other mediators or combinations of mediators.

Figure 5A:
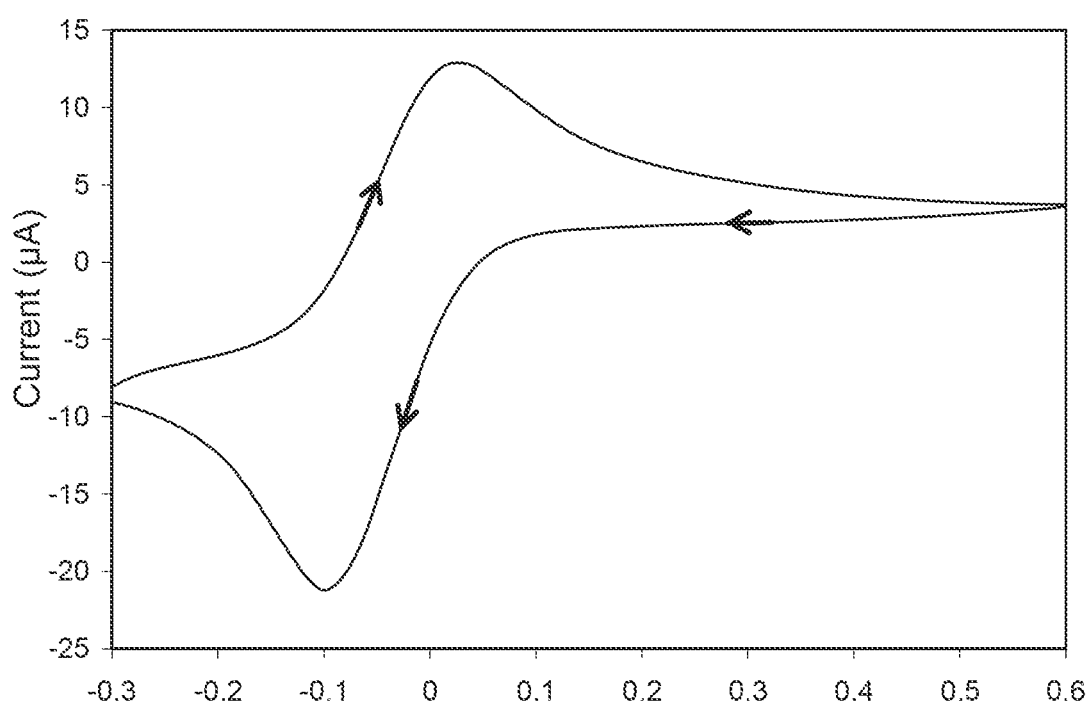
FIG. 5A depicts a cyclic scan from a sensor system.

FIG. 5A presents the data from a 25 mV/sec cyclic scan of a ferricyanide/ferrocyanide redox couple as a cyclic voltammogram, such as obtained from the CV-1 scan of FIG. 4E. The voltammogram is characterized by a forward current peak during the forward excitation of the scan from −0.3 V to +0.6 V indicating ferrocyanide oxidation and a reverse current peak during the reverse voltage scan from +0.6 V back to −0.3 V indicating ferricyanide reduction. The forward and reverse current peaks center around the formal potential $E^{0\prime}$ of the ferrocyanide/ferricyanide redox couple, when referenced to the counter electrode. In this aspect, the potential of the counter electrode is substantially determined by the reduction potential of ferricyanide, the major redox species present at the counter electrode.

While the potentials where the forward and reverse scans begin (the scan range) may be selected to include the reduced and oxidized states of the redox couple, the scan range may be reduced to shorten the analysis time. However, the scan range preferably includes the DLC region for the redox couple. For example, at a scan rate of 25 mV/sec, the concentration of the reduced [Red] and oxidized [Ox] species of the ferrocyanide/ferricyanide reversible redox couple and the resulting electrode potential are described by the Nernst equation as follows in Equation (1). Reversible redox couples are two redox species where the separation between the forward and reverse scans of the semi-integral is at most 30 mV at the half-height of the $si_{ss}$ transition. For example, in FIG. 6A the forward and reverse semi-integral scans for the ferricyanide/ferrocyanide redox couple in addition to the $si_{ss}$ transition height are shown. At the line where the half-height $si_{ss}$ transition line intersects the forward and reverse scan lines the separation between the lines is 29 mV, establishing the reversibility of the ferricyanide/ferrocyanide redox couple at the depicted scan rate.

$$E = E^{0\prime} + \frac{RT}{nF}\ln\frac{[Ox]}{[Red]} \underline{T = 25°\ C,\ E^{0\prime} +} \quad (1)$$

$$\underline{\frac{0.059}{n}\log\frac{[Ox]}{[Red]} n = 1 E^{0\prime}} + 0.059\log\frac{[Ox]}{[Red]}$$

In the Nernst equation, R is the gas constant of 8.314 Joul/(mole*K), F is the Faraday constant of 96,5000 Coul./equiv., n is the number of equivalents per mole, and T is the temperature in degrees Kelvin. When the potential at the working electrode is compared to its own redox potential, the formal potential $E^{0\prime}$ will become substantially zero and the equation collapses to:

$$E = 0.059\log\frac{[Ox]}{[Red]} = 0.059\log\frac{[Fe(CN)_6^{-3}]}{[Fe(CN)_6^{-4}]}. \quad (2)$$

From equation (2), when the ratio of the oxidized mediator to the reduced mediator changes by 10, the potential at the working electrode changes by about 60 mV. The reverse is also true. Thus, for ferricyanide [Ox] to ferrocyanide [Red] concentration ratios of 10:1, 100:1, 1000:1 and 10,000:1, the potential at the working electrode will be approximately 60, 120, 180, and 240 mV away from the zero potential, respectively.

Thus, when the ratio of ferricyanide to ferrocyanide is ~1000:1, a scan range of −180 mV to +180 mV would provide substantially complete oxidation of the reduced species at the working electrode. At 180 mV, the oxidation rate is limited by how fast the reduced form of the mediator can diffuse to the conductor surface, and from this potential forward, there exists a DLC region. Thus, if the reversing-point is set ~400 mV from the zero potential, ~200 mV of DLC region may be provided.

For reversible systems, it may be preferable to provide a scan range of from 400 to 600 mV, thus scanning from 200 to 300 mV on each side of the formal potential $E^{0\prime}$ of the redox couple. For quasi-reversible systems, it may be preferable to provide a scan range of from 600 to 1000 mV, thus scanning from 300 to 500 mV on each side of the formal potential $E^{0\prime}$ of the redox couple.

The larger scan range may be preferred for quasi-reversible systems because the DLC region may be smaller. In addition to redox couples that are inherently quasi-reversible, fast scans may cause a redox couple that is reversible at slow scan rates to demonstrate quasi-reversible behavior. Thus, it may be preferable to provide a larger quasi-reversible scan range for a reversible redox couple at fast scan rates.

Preferably, at least 25, 50, 100, 150, or 300 mV of DLC region is provided by the selected scan range. In another aspect, the reversing-point for a cyclic or acyclic scan is selected so that from 25 to 400 mV, from 50 to 350 mV, from 100 to 300 mV, or from 175 to 225 mV of DLC region is provided. For reversible systems, the reversing-point for a cyclic or acyclic scan may be selected so that from 180 to 260 mV or from 200 to 240 mV of DLC region is provided. For quasi-reversible systems, the reversing-point for a cyclic or acyclic scan may be selected so that from 180 to 400 mV or from 200 to 260 mV of DLC region is provided.

Figure 5B:
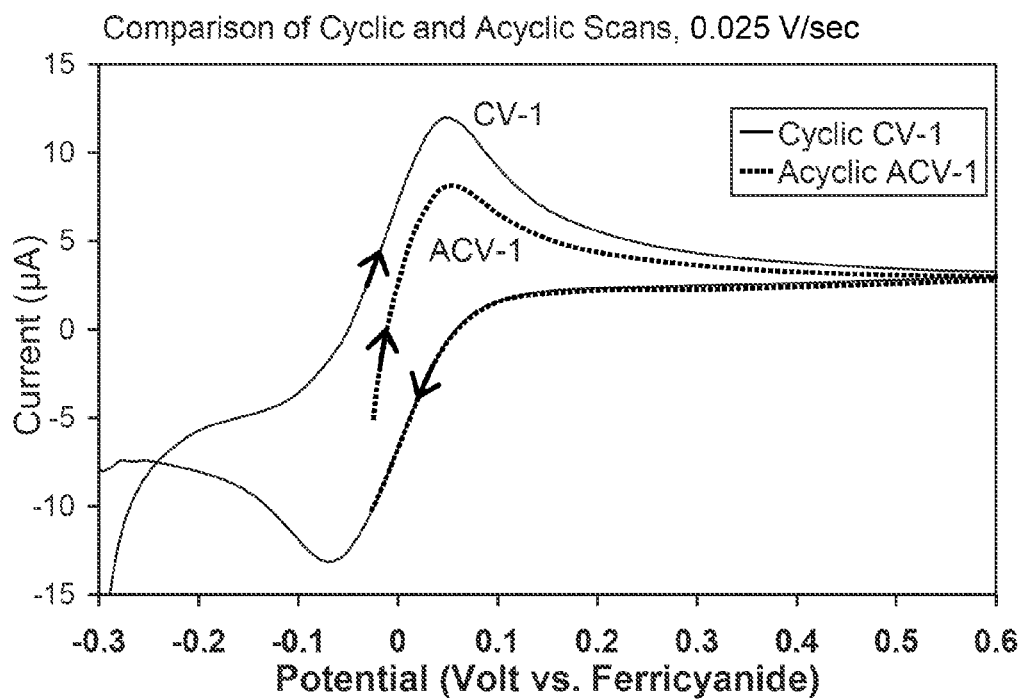
FIG. 5B compares a cyclic scan to an acyclic scan, where the forward excitation of the acyclic scan was started near the formal potential $E^{o'}$ for the redox couple.

Once the reversing-point is selected to provide the desired DLC region, the duration of the reverse scan may be selected for an acyclic scan. As can be seen in FIG. 5B, starting the forward scan and terminating the reverse scan at approximately −0.025 mV resulted in an acyclic scan, such as would be obtained from scan ACV-1 of FIG. 4E, which included more of the forward current peak than the reverse current peak. From the FIG. 5B comparison, while the peak currents obtained for the cyclic (CV-1) and acyclic (ACV-1) scans differ, the DLC region of the scans were nearly the same, especially with regard to the reverse scan.

Figure 5C:
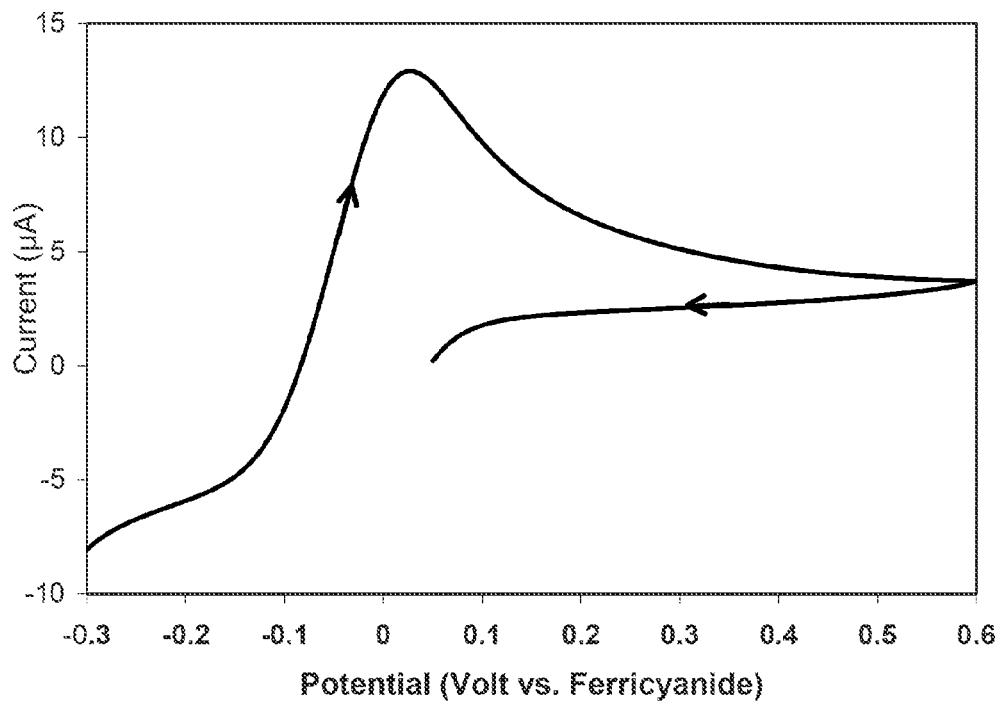
FIG. 5C shows an acyclic scan, where the reverse scan is terminated before the reverse current peak.

In another aspect, the reverse scan may be terminated before the reverse current peak is reached, as depicted in FIG. 5C. When the forward scan was started at a potential sufficiently negative, such as at −0.3 mV in FIG. 5C, to the middle of the potential range of the redox couple, such as −0.05 mV in FIG. 5C, the forward scan included the full range of the redox potential of the redox couple. A scan of this type would be obtained from the pulse CV-2 of FIG. 4E. Thus, by terminating the reverse excitation at a potential from 50 to 500 mV, from 150 to 450 mV, or from 300 to 400 mV negative from the reversing-point, for example, the reverse current peak may be excluded for the ferricyanide/ferrocyanide redox couple.

Similarly, the reverse scan also may be terminated before the reverse current peak is reached by terminating the scan when the reverse scan current deviates in value from the DLC. A change in the reverse scan current of at least 2%, 5%, 10%, or 25% may be used to indicate the beginning of the reverse scan current peak.

Figure 5D:
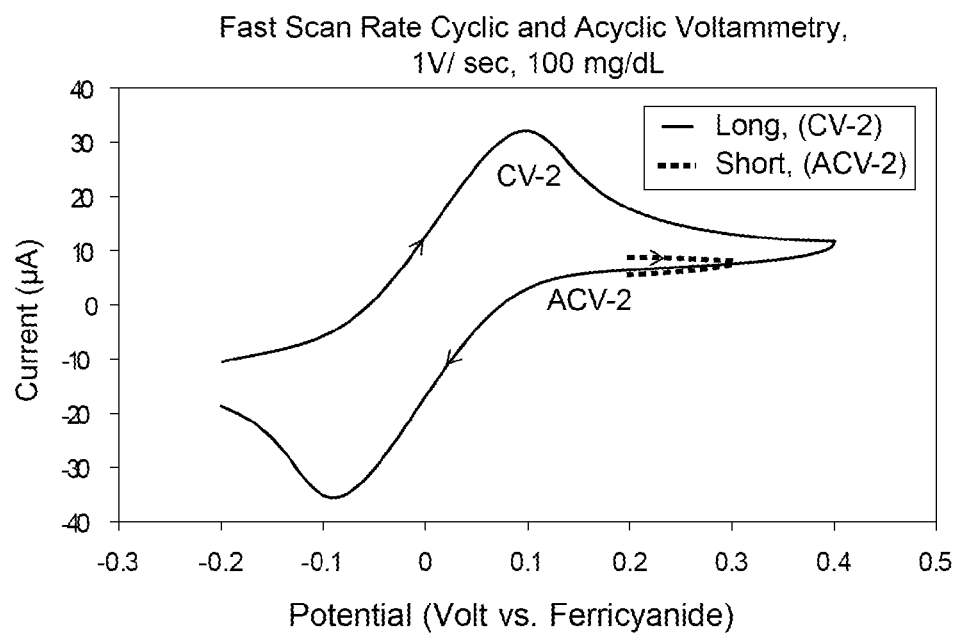
FIG. 5D shows a cyclic scan with an acyclic scan superimposed in the DLC region.

FIG. 5D compares a 1 V/sec cyclic voltammogram including the forward and reverse oxidation peaks of the redox couple with a 1 V/sec acyclic voltammogram that excludes the forward and reverse oxidation peaks of a redox couple. The acyclic scan had starting and ending points of 200 mV and a reversing-point of 300 mV, as would be provided from the ACV-2 acyclic scan represented in FIG. 5D. Preferable ranges for acyclic scans within the DLC region of the ferricyanide/ferrocyanide redox couple, which exclude the forward and reverse oxidation and reduction peaks, are from 10 to 200 mV, more preferably from 50 to 100 mV. While the cyclic voltammogram including the complete scan range significantly decayed after reaching the current peak, the acyclic voltammogram provided a substantially flat current region over the scan range. This current region may be directly correlated with the analyte concentration of the sample.

As seen in FIG. 5D, the current values recorded from the acyclic scan are numerically smaller than those from the cyclic scan, while the background current is lower for the acyclic scan. This beneficial reduction in background current was unexpectedly obtained without having to initiate the acyclic scan in the reduction peak portion of the cyclic scan. Thus, a fast and short acyclic scan within the DLC region of a redox couple may increase the measurement performance of the system due to a reduction in the background current, which may provide an increase in the signal-to-background ratio.

Figure 5E:
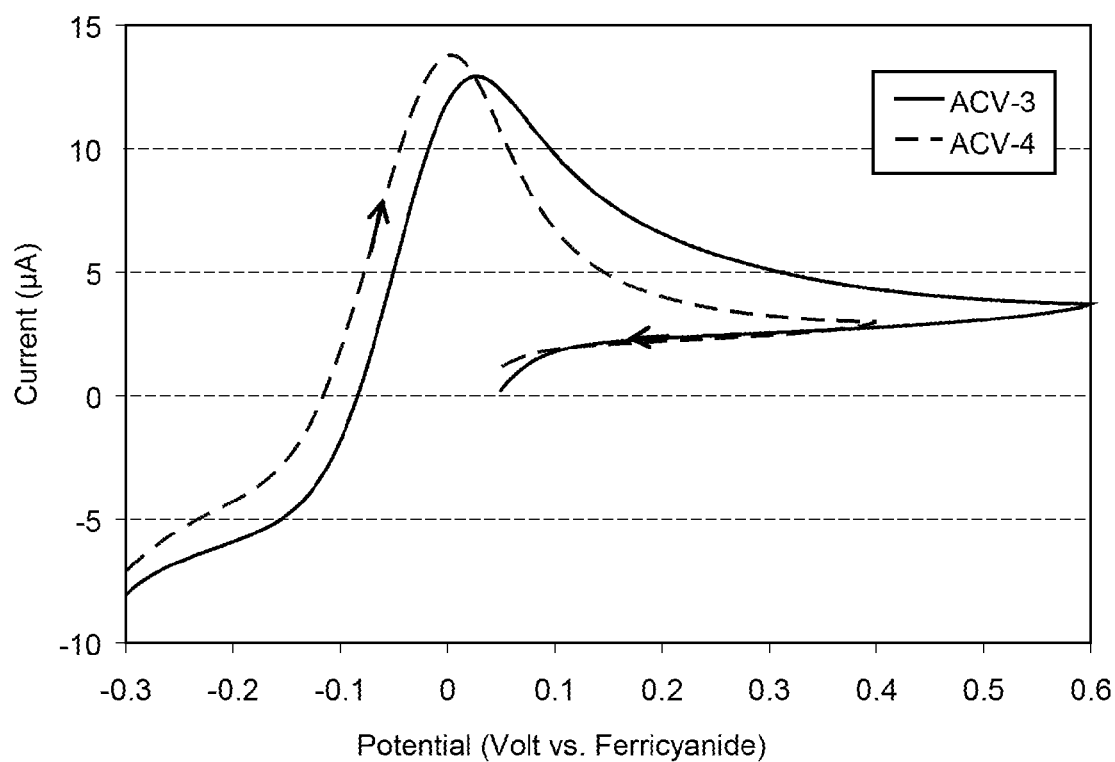
FIG. 5E depicts the output currents of an acyclic scan from the ACV-3 and ACV-4 acyclic scans of FIG. 4F.
Figure 5F:
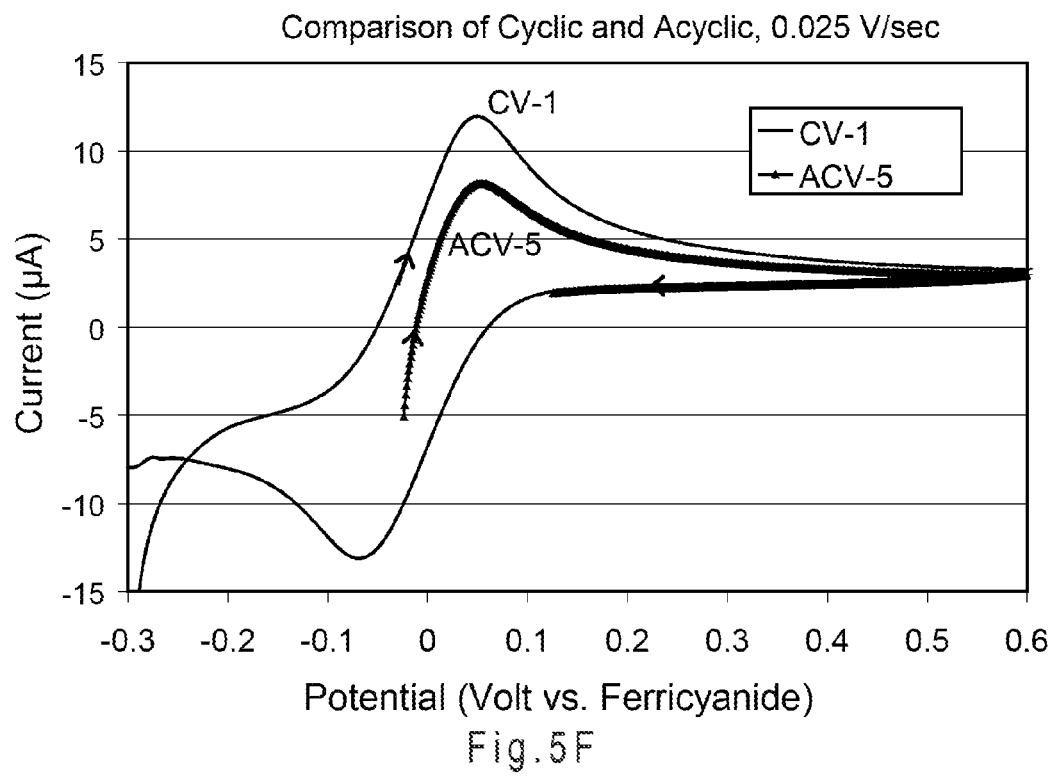
FIG. 5F compares output currents from cyclic and acyclic scans.

FIG. 5E shows that the steady-state portion of the current may be independent of the reversing point potential. FIG. 5F compares the output currents from the cyclic scan CV-1 from FIG. 4E with the output currents from the acyclic scan ACV-5 from FIG. 4F. The figures show that substantially similar steady-state currents may be obtained from different starting potentials.

Figure 6A:
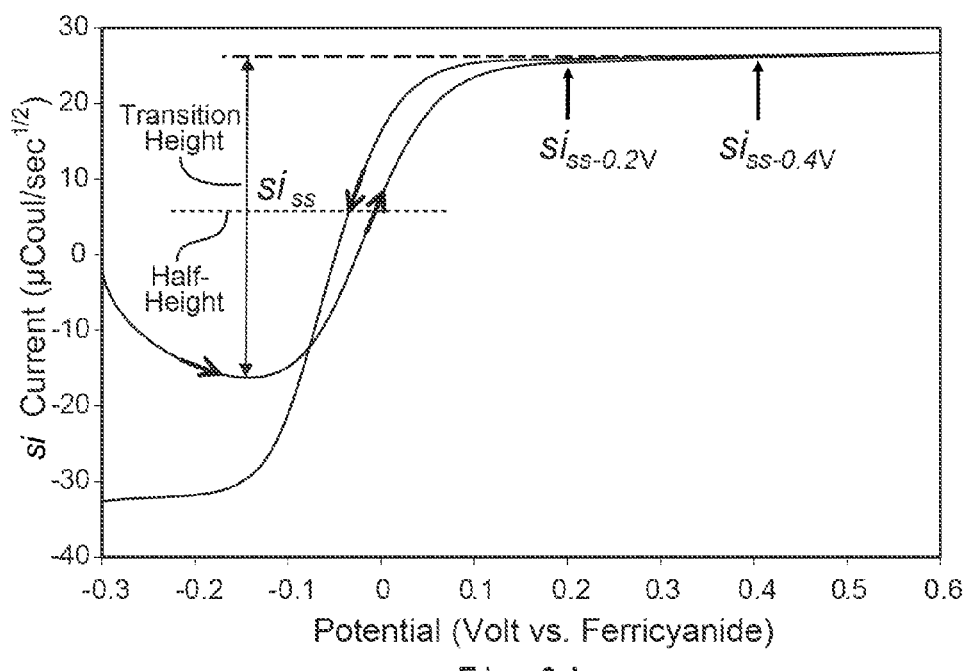
FIG. 6A is a graph of the semi-integral corresponding to the cyclic voltammogram of FIG. 5A.
Figure 6B:
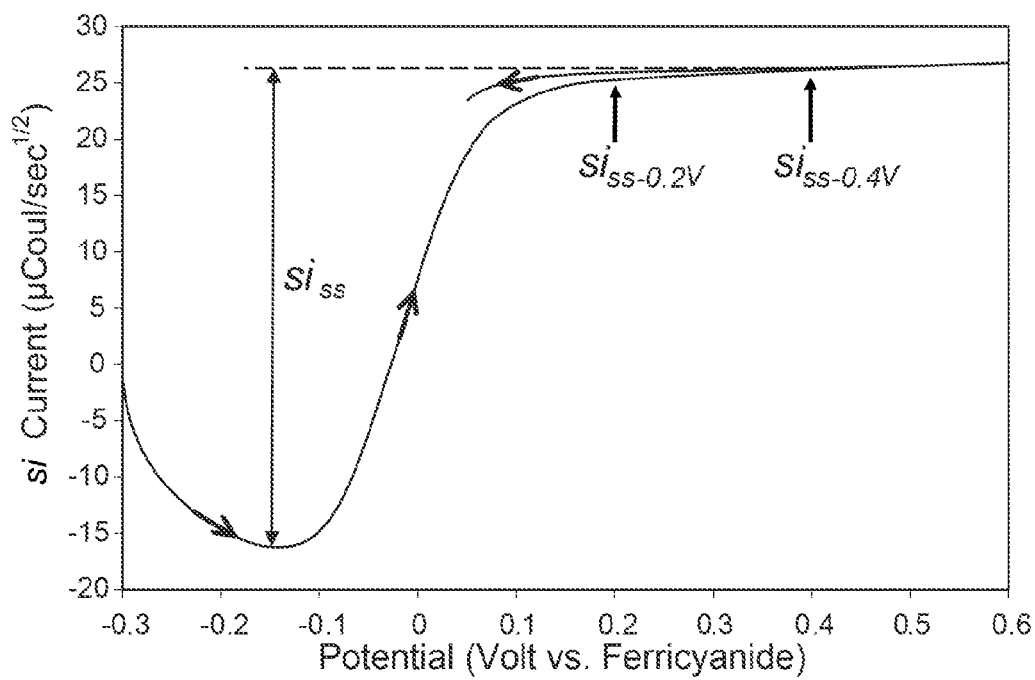
FIG. 6B presents the semi-integral of the output current data corresponding to the acyclic scan of FIG. 5C.
Figure 6C:
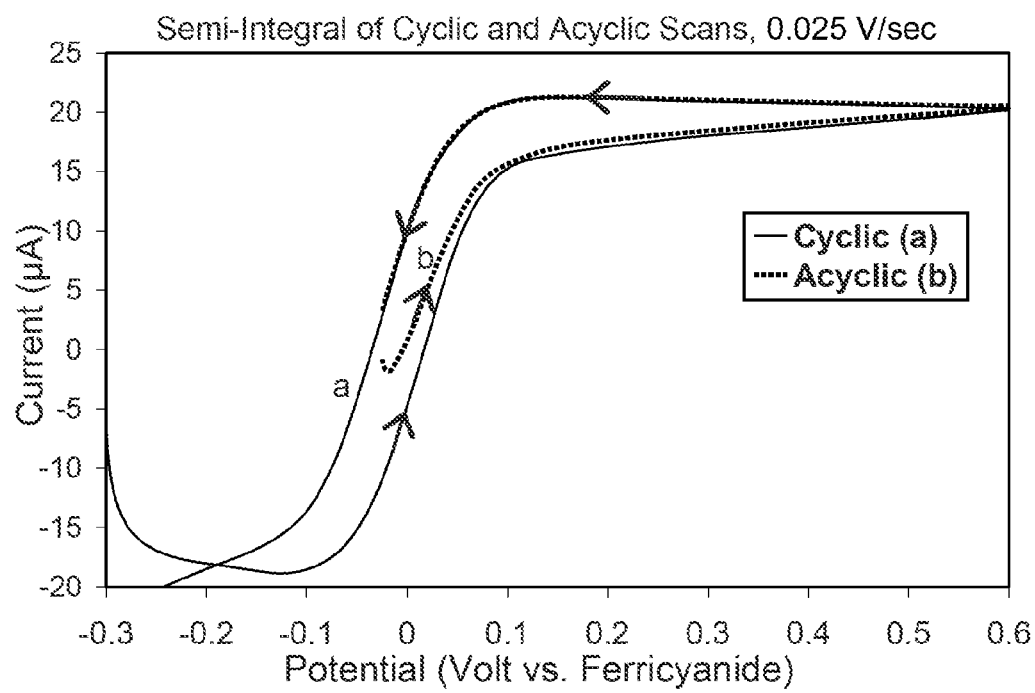
FIG. 6C presents the semi-integrals of the cyclic and acyclic scans of FIG. 5B.

FIG. 6A presents the semi-integral plot of the cyclic voltammogram from FIG. 5A where the flat region extending from about 0.1 V to 0.6 V defines the DLC region or the current plateau. This plateau region is embedded in the voltammetric output currents of FIG. 5A extended from the peak potential into the high potentials. Similarly, FIG. 6B presents the semi-integral plot of the acyclic voltammogram from FIG. 5C, where the reverse excitation terminated before initiation of the reverse current peak. FIG. 6C establishes that when the semi-integral of the cyclic and acyclic scans of FIG. 5B are plotted, the DLC region of the return scan was readily established, permitting an accurate current reading in as little as 50 mV from the reversing-point. Furthermore, the peak portion of the semi-integral plot was responsive to the hematocrit content of the sample and the magnitude of the peak may be quantitatively related to the hematocrit level.

Figure 6D:
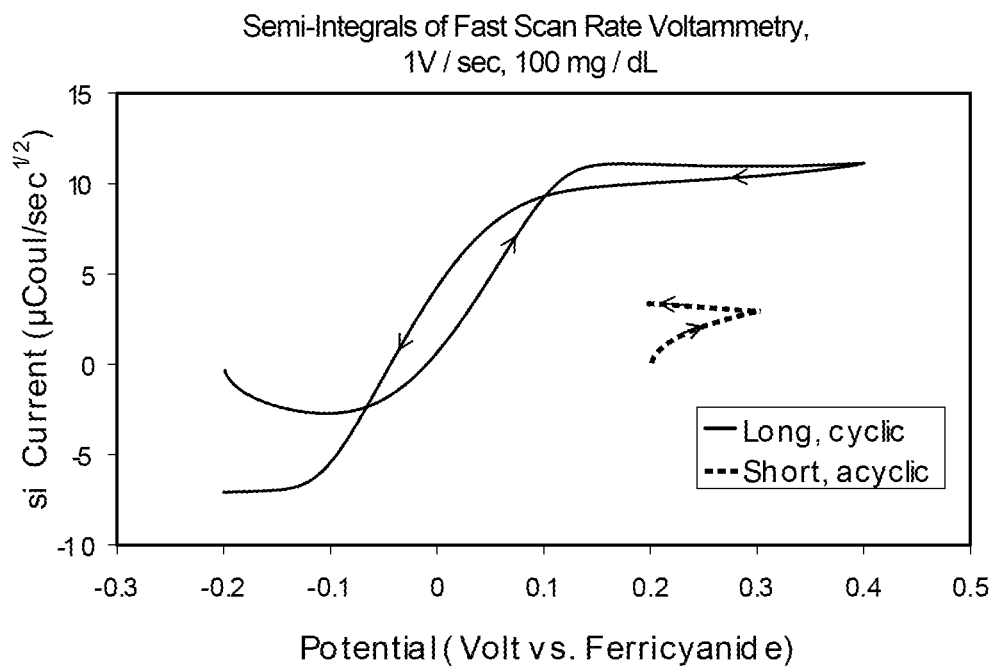
FIG. 6D shows the semi-integral and recorded current values for the acyclic scan of FIG. 5D.

FIG. 6D shows the semi-integrals for the cyclic and 200 to 300 mV acyclic scans of FIG. 5D. The shape of the si voltammogram from the short acyclic scan differs from the voltammogram of the cyclic scan because the region of oxidation-reduction transition is missing from the acyclic scan. By starting the acyclic scan in the DLC region, the background si current decreased at a faster rate in comparison to that observed for the cyclic voltammogram, thus improving the signal-to-background ratio for the acyclic scan. Furthermore, the reverse si current from the acyclic scan shows a plateau more accurately describing the analyte concentration of the sample than the forward si current. In this manner, the acyclic scan of the DLC region provided an increase in accuracy for the analysis when compared to the cyclic scan.

Cyclic and acyclic scans may provide multiple benefits in relation to linear scans. In one aspect, the portion of the reverse scan from the reversing-point to the point where the reverse current peak begins may be a better representation of the true DLC values than the DLC region of the forward scan. The DLC region of the reverse scan may be a more accurate representation of analyte concentration for quasi-reversible redox systems or at fast scan rates because the forward scan may not show a distinct DLC region.

Acyclic scans may have multiple advantages over cyclic scans including a shorter pulse width and a substantial decrease in the amount of mediator electrochemically converted to the measurable state. Thus, if the mediator is reduced in response to the analyte and electrochemically oxidized during measurement, terminating the reverse scan before the oxidized mediator is electrochemically reduced decreases the amount of reduced mediator in the sample not responsive to the analyte. Similarly, starting the forward scan at a potential above that at which the measurable species is reduced also may decrease the amount of reduced mediator in the sample not responsive to the analyte. Both acyclic scans may allow for a shorter analysis time, a significant benefit for the user.

Figure 7A:
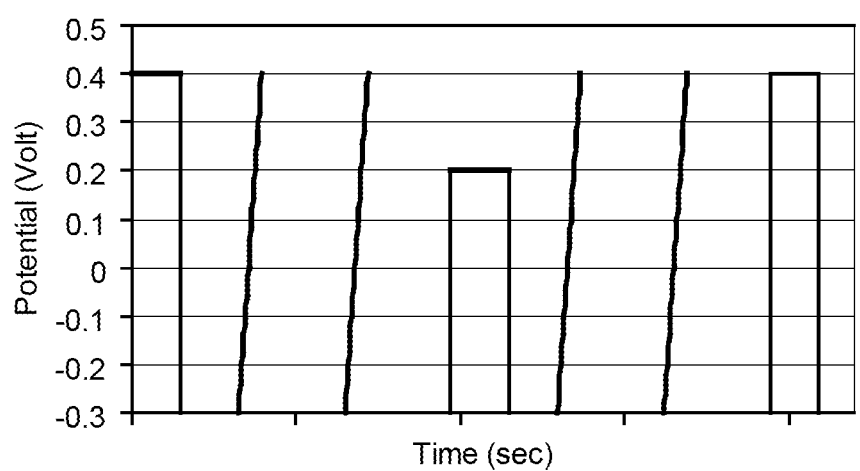
FIGS. 7A-7C represent input signals including amperometric and voltammetric duty cycles.
Figure 7B:
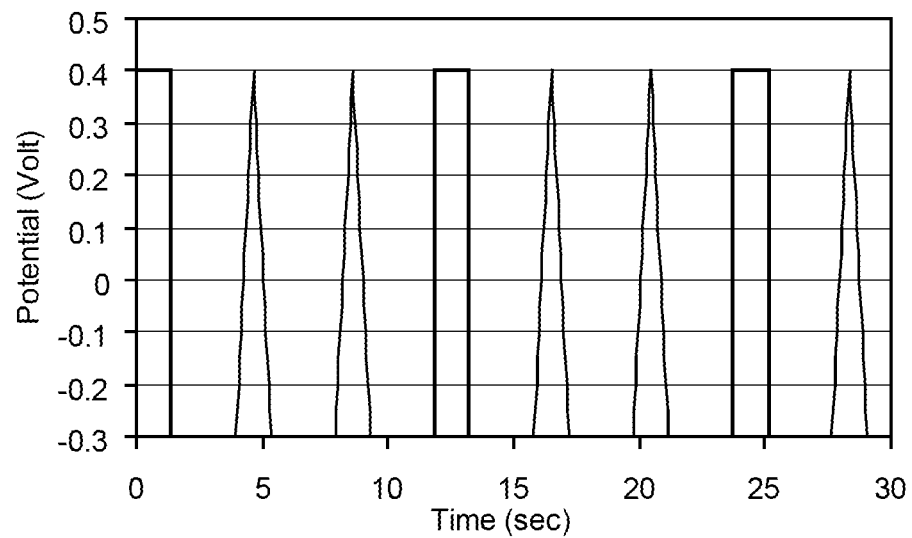
Figure 7C:
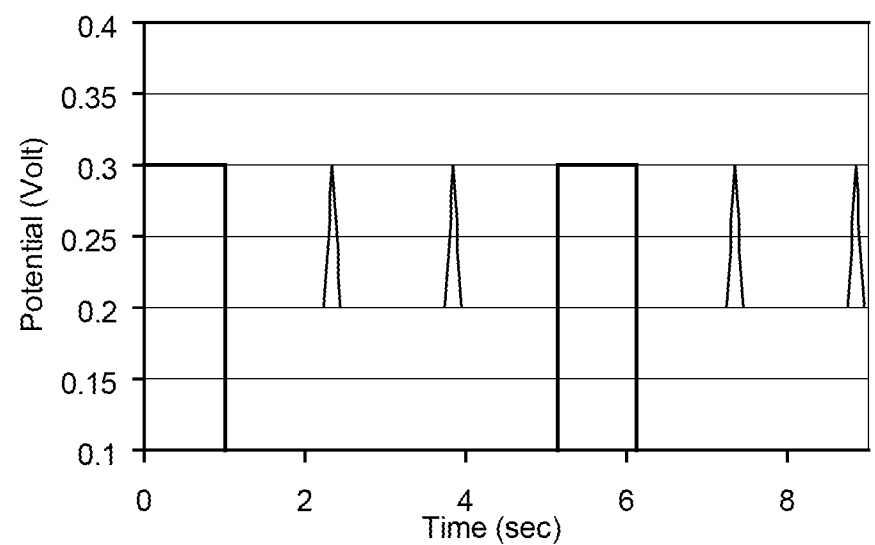

FIGS. 7A-7C represent input signals including amperometric and voltammetric duty cycles. The input signals also may include initial incubation periods and the like. FIG. 7A represents an input signal having a total of seven duty cycles, where three of the duty cycles include square-wave amperometric excitations of two different amplitudes, and four of the duty cycles include linear scans. The voltammetric scans are at a scan rate of 1 V/sec, requiring about 0.7 seconds to complete the scan from −0.3 V to +0.4 V. The pulse width of the voltammetric scans is approximately equivalent to that of the amperometric scans, which have a pulse width of about 1 second. The linear scans cover the potential range from the substantially reduced (−0.3 V) to the substantially oxidized (+0.4 V) form of the redox couple, presuming the working and counter electrodes include the same couple. The linear scan terminates at the substantially oxidized endpoint (+0.4 V) for the couple and does not reverse.

FIG. 7B represents an input signal having a total of eight duty cycles, where three of the duty cycles include square-wave amperometric excitations of substantially the same amplitude, and the remaining five duty cycles include cyclic scans, presuming the working and counter electrodes include the same mediator. The amperometric and cyclic scans have approximately the same scan rate of 1 V/sec, requiring about 1.4 seconds to complete the scan from −0.3 to +0.4 V and back to −0.3 V. The cyclic scans cover the potential range from the substantially reduced (−0.3 V) to the substantially oxidized (+0.4 V) form of the redox couple, presuming the working and counter electrodes include the same couple; however, unlike in FIG. 7A, the voltammetric scans include a reversing-point at the substantially oxidized (+0.4 V) form of the couple and return to the substantially reduced (−0.3 V) form.

FIG. 7C represents an input signal having a total of five duty cycles, where two of the duty cycles include square-wave amperometric excitations of substantially the same amplitude, and the remaining three duty cycles include acyclic scans, presuming the working and counter electrodes include the same mediator. The input signal of FIG. 7C also includes an acyclic scan as a terminal read pulse, as the excitation is not followed by a relaxation. The amperometric excitation and acyclic scans have approximately the same scan rate of 1 V/sec, requiring about 0.2 seconds to complete the scan from +0.2 V to +0.3 V and back to +0.2 V. As the voltammetric scans occur in the plateau region of the redox couple, the currents are substantially flat across the relatively short 0.1 V potential range of oxidation. Voltammetric scans of this type provide output signals including currents representing measurable species lacking the relatively fast amperometric decays, but having been excited for relatively short time periods. Output signals of this type may be preferred to increase the measurement performance of the system. Input signals having these and other duty cycle arrangements may be used to increase the measurement performance of the system.

Figure 8A:
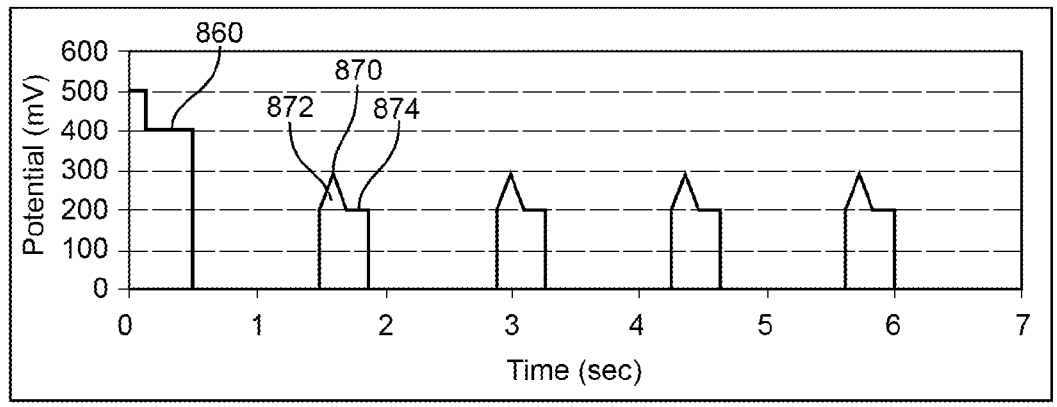
FIG. 8A represents an input signal having a total of five duty cycles, where a first pulse is a stepped-amperometric excitation and the following four pulses combine amperometric excitations and voltammetric scans into a single multi-excitation pulse.

FIG. 8A represents an input signal having a total of five duty cycles, where a first pulse 860 is a stepped-amperometric excitation and the following four pulses combine amperometric excitations and voltammetric scans into a single multi-excitation pulse 870. Each of the multi-excitation pulses includes an acyclic component 872 and an amperometric excitation component 874. While the acyclic scan components 872 are depicted first, they could follow the amperometric excitation components 874. Furthermore, more than one of each component could be included in the same pulse. Each of the pulses 860, 870 are followed by a relaxation to provide a duty cycle. A terminal read pulse could be used that is not followed by a relaxation. The pulse widths of the acyclic scan components 872 and the amperometric excitation components 874 are approximately equal; however, one could be longer. The acyclic scan portion of the pulse may occur in the plateau region of a redox couple. Output signals of this type may be preferred to increase the measurement performance of the system. Input signals having these and other duty cycle arrangements may be used to increase the measurement performance of the system.

Figure 8B:
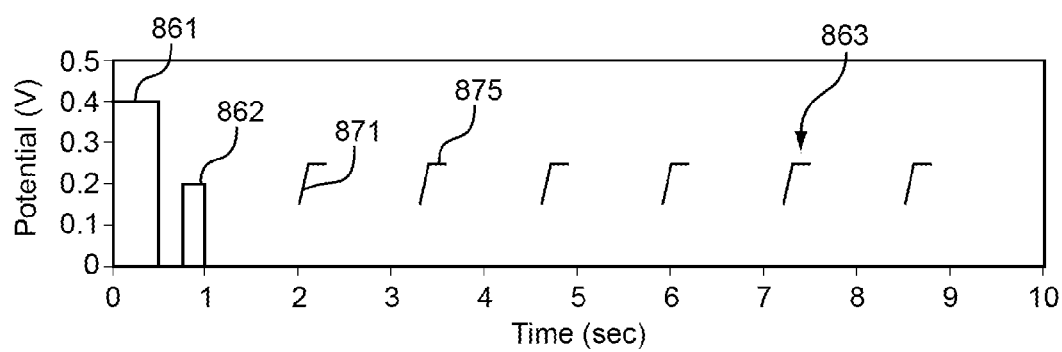
FIG. 8B represents an input signal having a total of eight duty cycles, where a first pulse and a second pulse are amperometric excitations and the following six pulses combine voltammetric scans and amperometric excitations into a single multi-excitation pulse.

FIG. 8B represents an input signal having a total of eight duty cycles, where a first pulse 861 and a second pulse 862 are amperometric excitations and the following six pulses combine voltammetric scans and amperometric excitations into a single multi-excitation pulse 870. Each of the multi-excitation pulses starts with a linear scan component 871 and transitions to an amperometric excitation component 875. While the linear scans 871 are depicted first, they could follow the amperometric excitations 875. Furthermore, more than one of each component could be included in the same pulse. Each of the pulses 861, 862, 863 is followed by a relaxation to provide a duty cycle. A terminal read pulse could be used that is not followed by a relaxation. The pulse widths of the linear scan components 871 and the amperometric excitation components 875 are approximately equal; however, one could be longer. The voltammetric scan component of the pulse may occur in the plateau region of a redox couple. Output signals of this type may be preferred to increase the measurement performance of the system. Input signals having these and other duty cycle arrangements may be used to increase the measurement performance of the system.

Input signals including multiple duty cycles provide the benefits of rapid analysis times and reductions in mediator background and the hematocrit effect. Amperometry provides output signals that may be used for temperature, underfill, and bias compensation, such as described in WO 2007/100651; U.S. Patent Doc. 2009/0095071, entitled "Underfill Detection System for a Biosensor;" and U.S. Provisional App. No. 61/012,716, filed Dec. 10, 2007, entitled "Slope-based Compensation," respectively. Other compensation methods also may be implemented using output currents from input signals including multiple duty cycles, such as those that adjust the input signal in response to the output signal, as described below.

Conversely, voltammetry provides output signals that may be integrated to strengthen the signal even with fast scan rates, thus providing an analyte responsive signal having an enhanced signal to noise ratio even at low analyte concentration levels in the sample. Other data treatments, including semi-integrals, derivatives, and semi-derivatives also may be advantageously used to process voltammetric output signals. A more detailed description of these data treatments may be found in WO 2007/040913. Voltammetry also may provide qualitative data about the ionizable species in the sample. Both the amperometric and voltammetric outputs can be used independently to determine one or more analyte concentrations. Either may be averaged or otherwise manipulated to increase the measurement performance of the system. The amperometric and voltammetric outputs for the same analyte also may be compared to determine a concentration value having enhanced accuracy and/or precision.

Figure 9A:
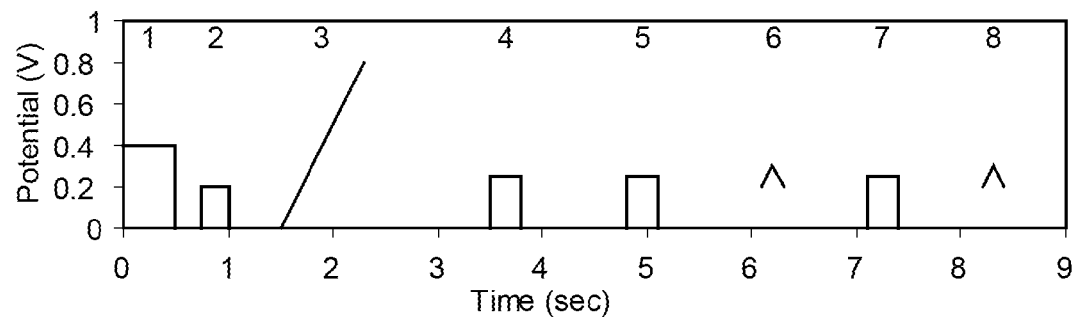
FIG. 9A represents an input signal having a total of eight duty cycles.

FIG. 9A represents an input signal having a total of eight duty cycles, where duty cycles 1, 2, 4, 5, and 7 have amperometric excitations, duty cycle 3 has a linear scan, and duty cycles 6 and 8 have acyclic scans. The number of each duty cycle is printed above the associated excitation in the figure. The amperometric excitation for duty cycle 1 was applied at a voltage of about 1 V, while the amperometric excitation for duty cycle 2 was applied at a voltage of about 0.2 V. The amperometric excitations for duty cycles 4, 5, and 7 were applied at a voltage of about 0.25 V. The linear scan rate was about 0.5 V/sec from 0 to about 0.7 V. The acyclic scan rate was about 1 V/sec from about 0.2 V to a reversing point of about 0.3 V and back. The acyclic scans were applied at potentials falling within the DLC region of the Structure I mediator, which has a DLC region from about 300 to about 500 mV. Other input signals having different numbers and types of duty cycles, potentials, and scan rates may be used. For example, a cyclic scan could be substituted for the linear scan.

Figure 9B:
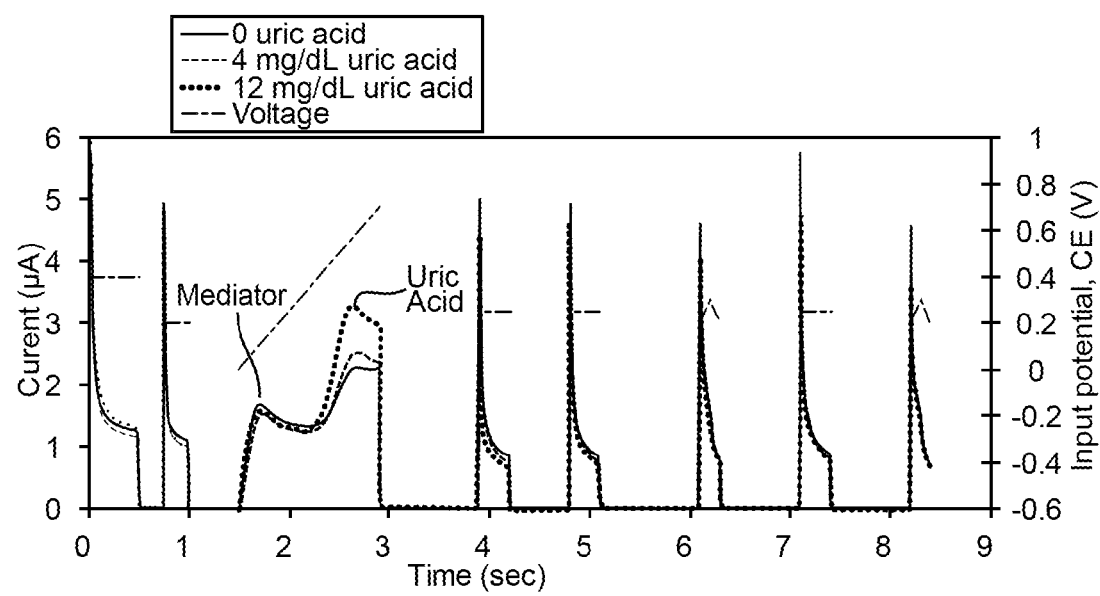
FIG. 9B plots the output currents as a function of time obtained when a measurement device applied the input signal of FIG. 9A to sensor strips including plasma, about 55 mg/dL of glucose as the analyte, and either 0, about 4 mg/dL, or about 12 mg/dL uric acid as an interferent.

FIG. 9B plots the output currents as a function of time obtained when a measurement device applied the input signal of FIG. 9A to sensor strips including plasma, about 55 mg/dL of glucose as the analyte, and either 0, about 4 mg/dL, or about 12 mg/dL uric acid as an interferent. Other analytes and interferents may be used. The sensor strip included working and counter electrodes, glucose dehydrogenase as an oxidoreductase, and the organic, two-electron mediator of Structure I, which has a redox potential about 200 mV lower than ferricyanide. Other sensor strip designs and reagents may be used.

The input signal voltages at the working electrode relative to the counter electrode corresponding to the output currents are represented by flat (amperometric) or angled lines (voltammetric) superimposed to the right or above the output currents of each duty cycle for clarity. As seen in the currents obtained from the linear scan, the left shoulder of the output currents from the linear scan are responsive to the mediator concentration of the sample, and the right shoulder of the output currents from the linear scan are responsive to the uric acid concentration of the sample.

Figure 9C:
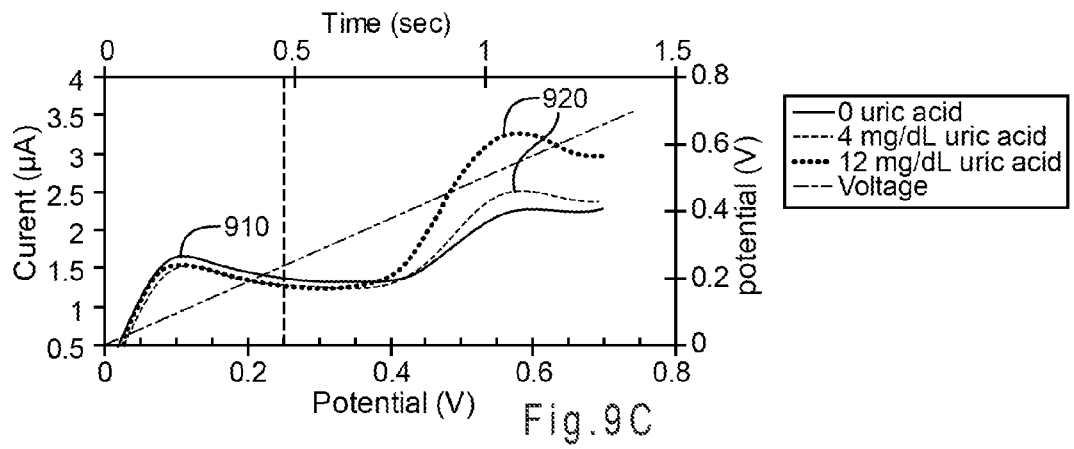
FIG. 9C and FIG. 9D plot the output currents versus potential for linear and acyclic scans.
Figure 9D:
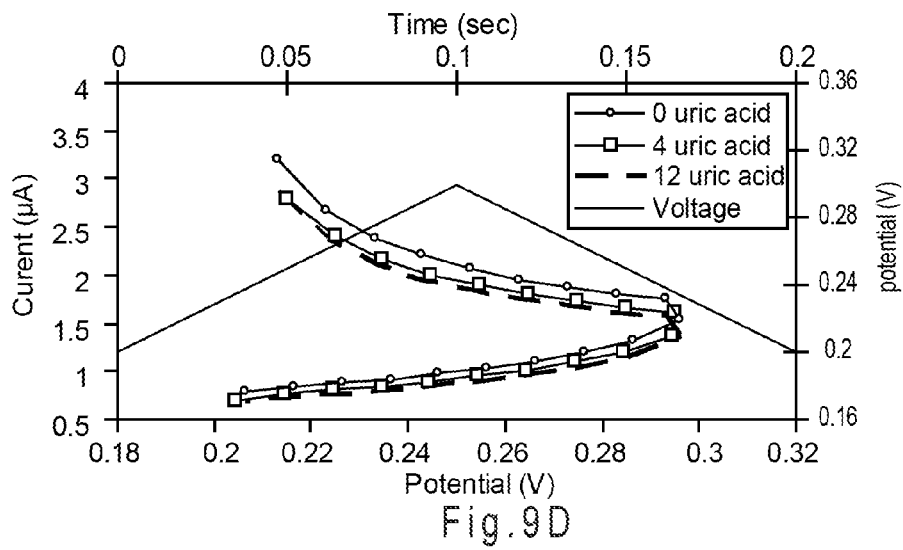

FIG. 9C and FIG. 9D plot the output currents versus potential for the linear scan of duty cycle 3 and the acyclic scan of duty cycle 6, respectively. The dashed vertical line in FIG. 9C indicates the 0.25 V potential used for the amperometric excitations of duty cycles 4, 5, and 7. In FIG. 9C, peak 910 is attributable to oxidation of the mediator and is responsive to the analyte, while peak 920 is attributable to uric acid oxidation and is responsive to the interferent. The output currents show that a valley occurs at about 0.3 to 0.4 V between the peak attributable to the mediator at about 0.18 V and the peak attributable to uric acid at about 0.58 V, which allows the system to determine that at least two contributing ionizable species are present in the sample. Derivatives of the output currents from the linear scan may be used to determine the peaks and valleys as the derivatives of the output current values would be positive or negative as the currents increase or decrease, respectively. One method of using derivatives to determine the peaks and valleys is the sequential differentiation of data points from beginning to ending, for instance $x_n-x_{n-1}$, or $x_2-x_1$, $x_3-x_2$, $x_4-x_3$ . . . . Thus, as the differentials change sign from positive to negative in a finite range, a peak is indicated, or a valley is indicated when the differential sign changes from negative to positive. Other mediators and interferents may provide different peaks and valleys. Other mathematical methods may be used to determine the peaks and valleys in the output currents.

By using potentials of less than about 0.4 V for the amperometric excitations or acyclic scans with the Structure I mediator, current values attributable to the uric acid interferent may be reduced or substantially eliminated. Thus, the system can use the output currents from the linear scan of the third duty cycle to adjust the potential of one or more amperometric excitations or acyclic scans, thereby reducing output currents responsive to an interferent.

With regard to the currents obtained from the linear scan of FIG. 9B, the measurement device applied the amperometric excitations of duty cycles 5 and 7 at about 0.25 V to substantially exclude uric acid interference. Thus, using a correlation equation or other means to relate the output currents from amperometric duty cycles 5 and/or 7 with the analyte concentration of the sample provides an increase in measurement performance and a reduction in uric acid interferent bias in comparison to an analysis where the potential exceeds about 0.3 V. The system can make other adjustments to the amperometric excitations or acyclic scans in response to the output currents from the linear scan to improve the measurement performance of the system.

Alternatively, if uric acid were the analyte of interest, the output currents from the linear scan may be used to adjust the potential of one or more subsequent amperometric excitations or acyclic scans to a potential of about 0.6 V, thus obtaining output currents responsive to the mediator and the uric acid. The output current values obtained from potentials of less than about 0.4 V could then be subtracted from the output current values obtained at about 0.6 V to obtain the current values substantially responsive to the uric acid concentration, while excluding the output current values substantially responsive to the mediator. This comparison through subtraction or other methods may be performed on the output current values or on concentration or other values determined from the output current values using correlation equations and the like.

As ionizable species having lower oxidation potentials produce output currents at lower and higher potentials, but ionizable species having higher oxidation potentials do not significantly produce output currents at lower potentials, the concentrations of one or more ionizable species may be determined by subtraction or related mathematical techniques that remove the output currents of one or more lower potential species from higher potential species. Thus, the system can determine the concentration of one or more ionizable species in the sample and report or use the determined values to correct reported concentration values.

In FIG. 9D, as the potential of the acyclic scan of duty cycle 6 was from about 0.2 V to about 0.3 V and back, the output currents responsive to the uric acid interferent were substantially eliminated. This was established by the substantial overlap of the output currents from the three acyclic scans. Thus, the output currents from acyclic scans with scan ranges from about 0.2 V to about 0.3 V and back were not substantially affected by the uric acid interferent and could be correlated with the concentration of the mediator, and thus the analyte, in the sample.

Figure 9E:
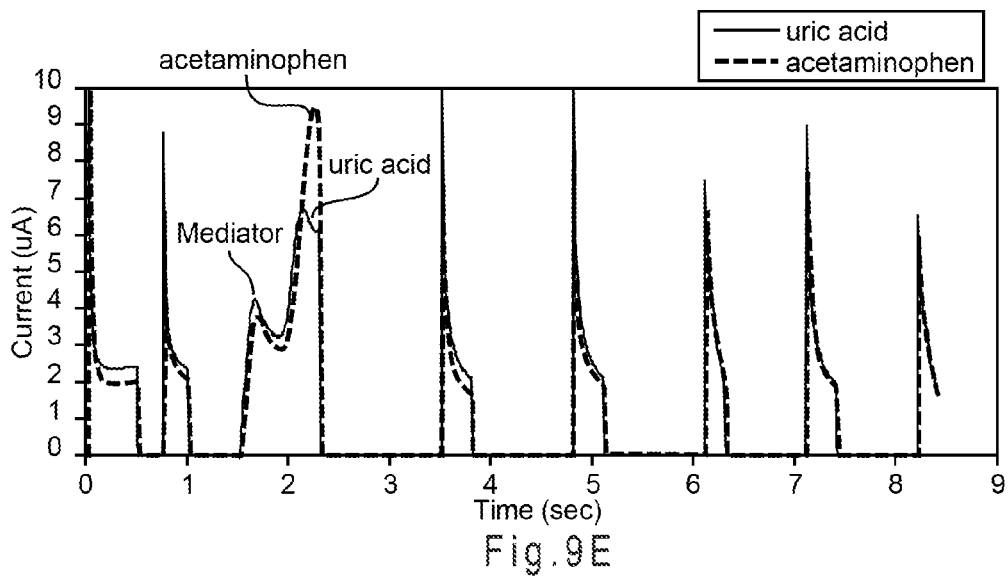
In FIG. 9E, the analysis of FIG. 9B was repeated with a plasma sample including about 110 mg/dL glucose, uric acid as naturally occurring in plasma, and about 8 mg/dL acetaminophen, as an additional interferent.
Figure 9F:
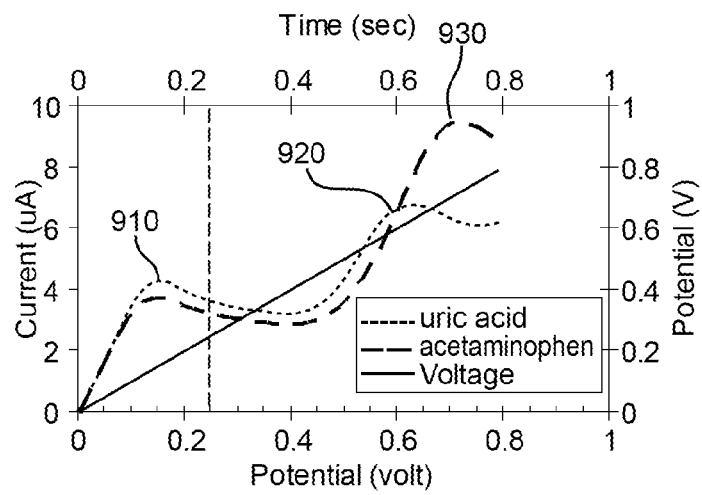
FIG. 9F depicts the detail of the linear scan of the third duty cycle revealing three separate peaks corresponding to the mediator, uric acid, and acetaminophen, respectively.
Figure 9G:
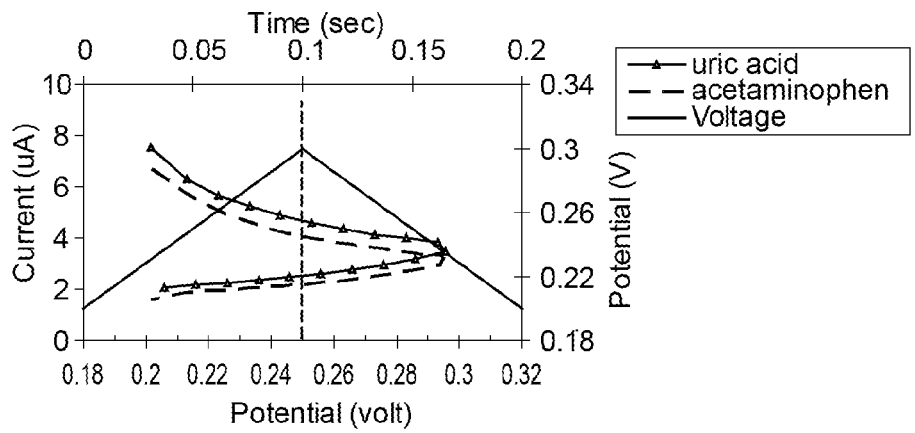
FIG. 9G depicts that as the potential of the acyclic scan changes from about 0.2 to about 0.3 V and back, output current values attributable to the uric acid and acetaminophen interferents were substantially eliminated.

In FIG. 9E, the analysis as previously described with regard to FIG. 9B was repeated with a plasma sample including about 110 mg/dL glucose, uric acid as naturally occurring in plasma, and about 8 mg/dL acetaminophen, as an additional interferent. In FIG. 9F, the detail of the linear scan of the third duty cycle reveals three separate peaks, 910, 920, and 930, corresponding to the mediator, uric acid, and acetaminophen, respectively. In FIG. 9G, as the potential of the acyclic scan changes from about 0.2 to about 0.3 V and back, output current values attributable to the uric acid and acetaminophen interferents were substantially eliminated. As previously discussed with regard to FIG. 9D, the single ionizable species contributing to the output currents is reflected by the substantial overlap of the output currents from the two acyclic scans. Thus, the output currents from acyclic scans with scan ranges from about 0.2 V to about 0.3 V and back were not substantially affected by the uric acid and acetaminophen interferents and could be correlated with the concentration of the mediator, and thus the analyte, in the sample.

Figure 10A:
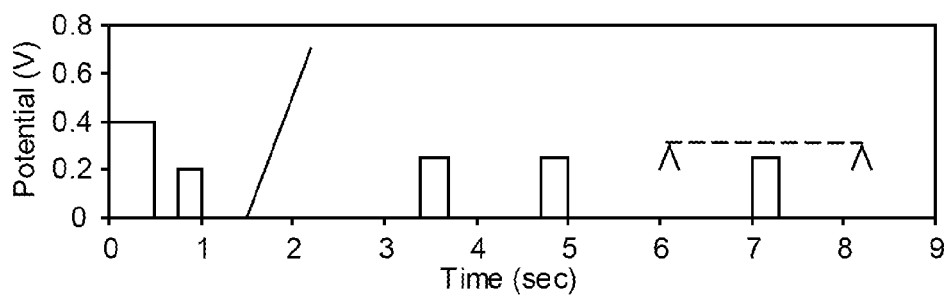
FIG. 10A represents an input signal having a total of eight duty cycles.

FIG. 10A represents an input signal having a total of eight duty cycles, where duty cycles 1, 2, 4, 5, and 7 have amperometric excitations, duty cycle 3 has a linear scan, and duty cycles 6 and 8 have acyclic scans. The amperometric excitation for duty cycle 1 was applied at a voltage of about 0.4 V, while the amperometric excitation for duty cycle 2 was applied at a voltage of about 0.2 V. The amperometric excitations for duty cycles 4, 5, and 7 were applied at a voltage of about 0.25 V. In comparison to FIG. 9A, the scan rate of the linear scan of FIG. 10A was at a faster rate, about 1 V/sec, while covering the same scan range from 0 to about 0.7 V. The acyclic scans were applied at a rate of about 1 V/sec from about 0.2 V to a reversing point of about 0.3 V and back, thus having a pulse width of about 0.1 V. Other input signals having different numbers and types of duty cycles, potentials, and scan rates may be used. For example, a cyclic scan could be substituted for the linear scan.

Figure 10B:
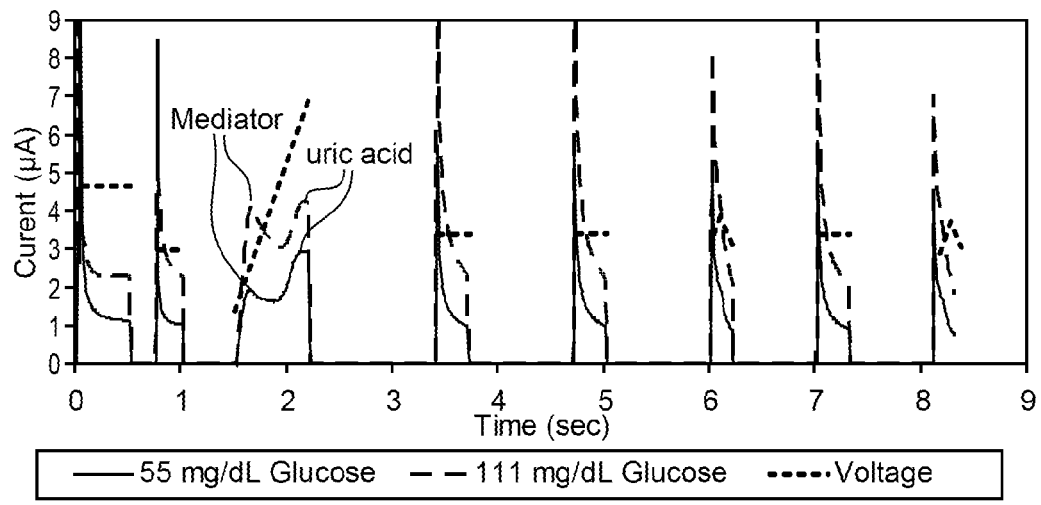
FIG. 10B plots the output currents as a function of time obtained when a measurement device applied the input signal of FIG. 10A to sensor strips including plasma, about 55 mg/dL or about 111 mg/dL of glucose as the analyte, and no additional uric acid.

FIG. 10B plots the output currents obtained as a function of time when a measurement device applied the input signal of FIG. 10A to sensor strips including plasma, about 55 mg/dL or about 111 mg/dL of glucose as the analyte, and no additional uric acid. Other analytes and may be used. The sensor strip included working and counter electrodes, glucose dehydrogenase as an oxidoreductase, and used the organic, two-electron mediator of Structure I. The input signal voltages at the working electrode relative to the counter electrode corresponding to the output currents are represented by flat (amperometric) or angled lines (voltammetric) superimposed to the right or above the output currents of each duty cycle for clarity. While additional uric acid was not added to the samples, the right shoulder of the output currents from the linear scan establishes that uric acid is naturally found in blood.

Figure 10C:
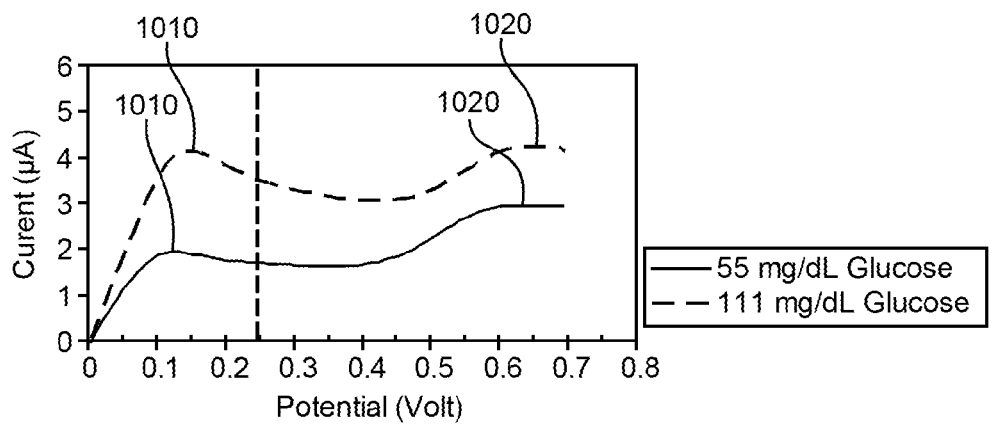
FIG. 10C and FIG. 10D plot the output currents versus potential for linear and acyclic scans.
Figure 10D:
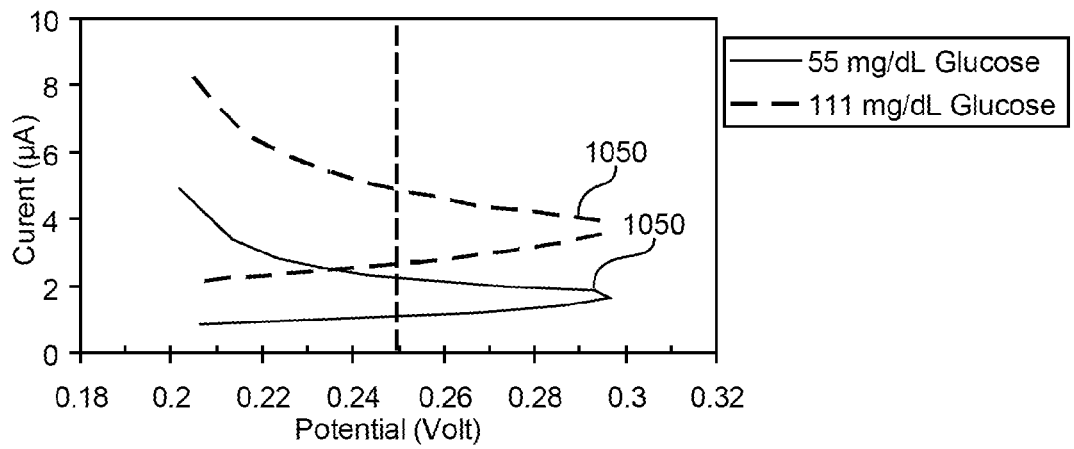

FIG. 10C and FIG. 10D plot the output currents versus potential for the linear scan of duty cycle 3 and the acyclic scan of duty cycle 8, respectively. The dashed vertical line in FIG. 10C indicates the 0.25 V potential used for the amperometric excitations of duty cycles 2, 4, 5, and 7. In FIG. 10C, peaks 1010 are attributable to oxidation of the mediator, and are responsive to the analyte, while peaks 1020 are attributable to another oxidizable species, likely uric acid, as previously discussed. Both mediator peaks 1010 reach a maxima before 0.15 V at the working electrode in relation to the counter electrode. The output currents show that a valley occurs at about 0.3 to 0.4 V between the peak attributable to the mediator at about 0.15 V and the peak attributable to uric acid at about 0.6 V, which as previously discussed, allows the system to determine that at least two ionizable species are contributing to the output currents and are present in the sample.

FIG. 10D showed that the acyclic scan of duty cycle 6 produced output currents that were separated with regard to the X-axis, allowing for the differing concentrations of the mediator, and thus the analyte, to be determined. As the amperometric excitations were applied at 0.25 V, the measurement device also may determine the analyte concentration of the sample from the output currents obtained from one or more of the amperometric duty cycles.

Figure 10E:
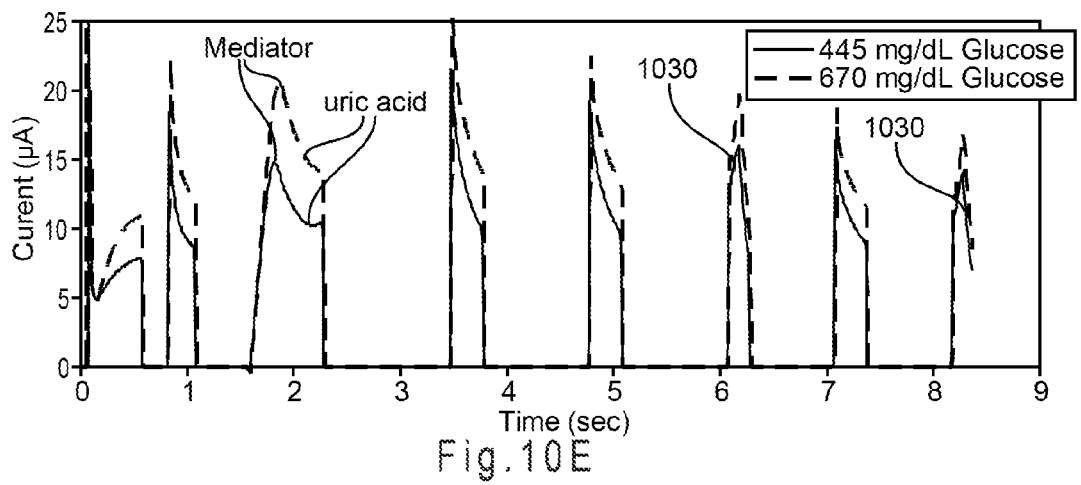
FIG. 10E plots the output currents as a function of time obtained when a measurement device applied the input signal of FIG. 10A to sensor strips including plasma, about 445 mg/dL or about 670 mg/dL of glucose as the analyte, and no additional uric acid.

FIG. 10E plots the output currents obtained as a function of time when a measurement device applied the input signal of FIG. 10A to sensor strips including plasma, about 445 mg/dL or about 670 mg/dL of glucose as the analyte, and no additional uric acid. In contrast to FIG. 10B, FIG. 10E depicts non-linear output currents from the acyclic scans of duty cycles 6 and 8, as the output currents from the forward excitations of the acyclic scans increase with potential. This increase with potential may be seen as the relatively flat, but still increasing, portion 1030 of the output currents obtained before the reversing point of the acyclic scans of duty cycles 6 and 8.

Figure 10F:
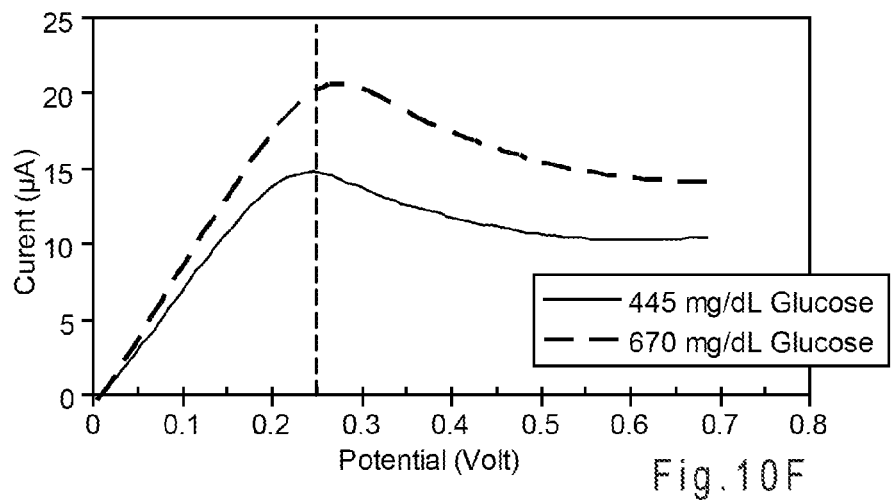
FIG. 10F and FIG. 10G plot the output currents verses potential for linear and acyclic scans.
Figure 10G:
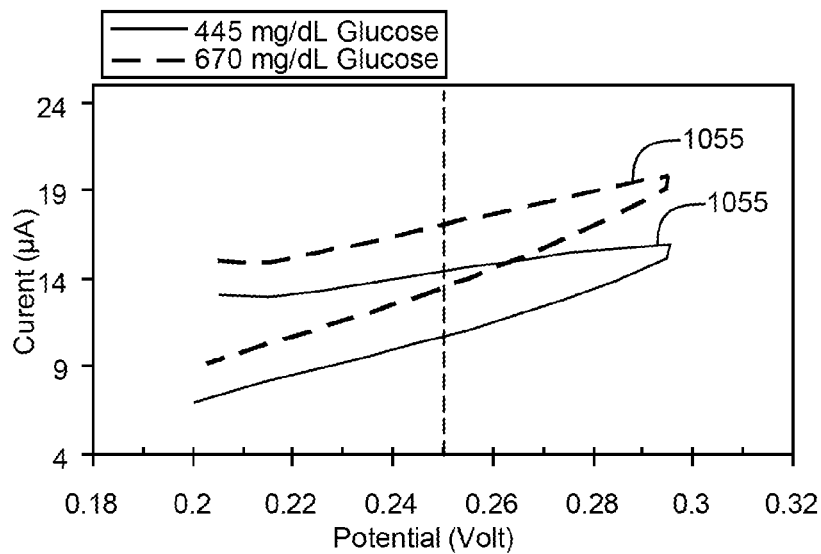

FIG. 10F and FIG. 10G plot the output currents verses potential for the linear scan of duty cycle 3 and the acyclic scan of duty cycle 6, respectively. The dashed vertical lines in FIG. 10F and FIG. 10G indicate the 0.25 V potential used for the amperometric excitations of duty cycles 4, 5, and 7. In contrast to FIG. 10C, which provided the results from the lower 55 and 111 mg/dL glucose concentrations, in FIG. 10F the oxidation peaks of the mediator responsive to the higher 445 and 670 mg/dL glucose concentrations have shifted significantly to the right in relation to the 0.25 V potential. As the peak redox potential observed in FIG. 10F (about 0.28 V for the 670 mg/dL sample) is greater than the potential of the amperometric excitations, the output currents obtained from the amperometric excitations, such as those obtained from duty cycles 4 and 5 in FIG. 10E, will have a non-linear response.

As the DLC region of the mediator has shifted to a higher potential, the 0.2 V to 0.3 V range of the acyclic scans occur substantially before and/or during the oxidation peak of the mediator. Thus, the output currents from acyclic scan duty cycles 6 and 8 occur substantially after the oxidation peak of the mediator in FIG. 10B and substantially before and/or during the oxidation peak of the mediator in FIG. 10E. As the acyclic scan range of FIG. 10E does not substantially fall in the DLC region of the mediator after the oxidation peak, instead falling within the peak region, the output currents obtained from the forward excitation of the acyclic scans (potential increasing) increase with the increasing input potential. Thus, the output currents obtained from the acyclic scans of duty cycles 6 and 8 also will have a non-linear response.

The system may detect a non-linear response from the slopes of the output currents obtained from the forward excitation of acyclic scans. A comparison of the output currents 1050 from the forward acyclic scan lines of FIG. 10D with the output currents 1055 from the forward acyclic scan lines of FIG. 10G, show that the output currents 1055 of FIG. 10G had a substantially positive slope in relation to the output currents 1050 of FIG. 10D. This established that for the higher 445 and 670 mg/dL glucose concentrations, the output currents obtained from the acyclic scans are not substantially from the DLC region of the mediator, but are instead responsive to the changing potential of the acyclic scan. Thus, the forward scan portion (potential increasing) of the acyclic scans can provide similar qualitative data as obtained from the linear scans—allowing the acyclic scans to provide output currents that the can be used to determine the presence of non-linear response at one or more potentials.

Depending on the severity of the non-linear response, the system may end the analysis or adjust the potential of amperometric excitations and/or acyclic scans in response to the output currents obtained from one or more voltammetric scans to reduce the non-linearity of the currents obtained from the adjusted amperometric excitations and/or acyclic scans. In this manner the system may adjust the potential of amperometric and/or acyclic scans into the DLC region of one or more ionizable species.

After determining the peak oxidation current for one or more ionizable species, the operating potential for subsequent excitations may be adjusted to be at least 50 mV or at least 100 mV higher than the potential at the oxidation peak. This adjustment may reduce the non-linearity of the output currents obtained from the subsequent excitations and increase the measurement performance of the system. Thus, with regard to the relatively high glucose concentrations of FIG. 10E through 10G, the data from the linear and/or acyclic scans may be used to increase the input potential of subsequent amperometric excitations and/or the starting potential of subsequent acyclic scans to greater than about 0.3 V to reduce the non-linearity of the output currents. Other amperometric input potentials may be used to reduce the non-linearity of the output currents depending on the system, sample, sensor strip, and the like.

Figure 11A:
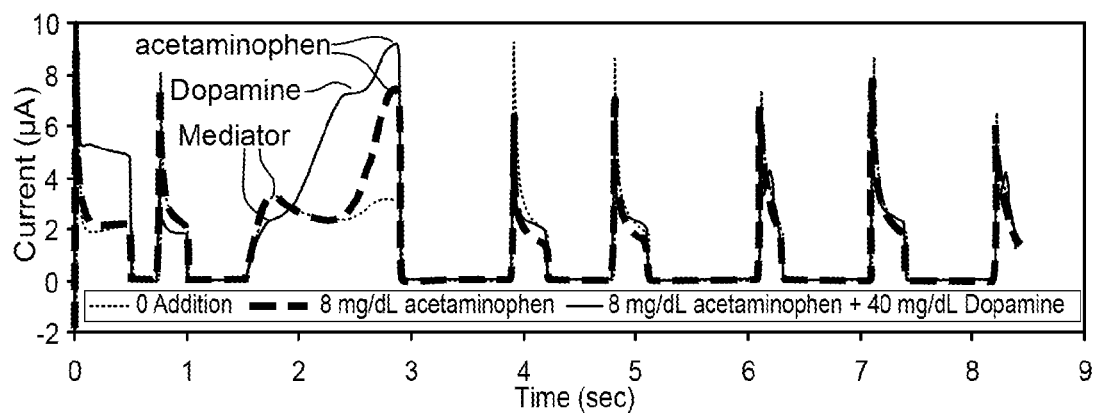
FIG. 11A plots the output currents as a function of time obtained when a measurement device applied the input signal of FIG. 9A to sensor strips including plasma, about 111 mg/dL of glucose as the analyte, and either 8 mg/dL acetaminophen or 8 mg/dL of acetaminophen in combination with 40 mg/dL dopamine as interferents.

In FIG. 9 and FIG. 10 uric acid and acetaminophen interferents were used that have oxidation potentials that do not substantially overlap with the oxidation potential of the Structure I, II, or III mediators. In contrast, FIG. 11A plots the output currents obtained as a function of time when a measurement device applied the input signal of FIG. 9A to sensor strips including plasma, about 111 mg/dL of glucose as the analyte, and either 8 mg/dL acetaminophen or 8 mg/dL of acetaminophen in combination with 40 mg/dL dopamine as interferents. Other analytes and interferents may be used. The oxidation potential of dopamine is slightly higher than that of the Structure I, II, or III mediators and overlaps with the oxidation potential of acetaminophen. The sensor strip included working and counter electrodes, glucose dehydrogenase as an oxidoreductase, and the organic, two-electron mediator of Structure I. Other sensor strip designs and reagents may be used.

Figure 11B:
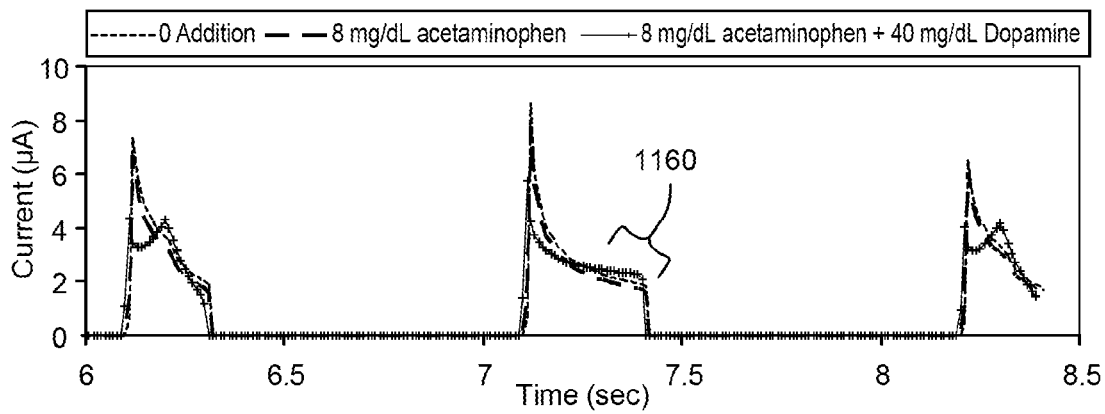
FIG. 11B provides expansions of the output currents recorded from the acyclic scans of duty cycles 6 and 8 and from the amperometric excitation of duty cycle 7 of FIG. 11A.

FIG. 11B provides expansions of the output currents recorded from the acyclic scans of duty cycles 6 and 8 and from the amperometric excitation of duty cycle 7. As previously discussed, the acetaminophen interferent is not substantially visible in the current values recorded from the amperometric excitation of duty cycle 7, and is not adversely affecting the measurement performance of the system with relation to analyte concentrations determined from this amperometric duty cycle. However, the current values recorded from the amperometric excitation of duty cycle 7 show a relatively small contribution 1160 from dopamine at the right of the decay. Thus, a glucose concentration determined from this peak for a sample including acetaminophen would show substantially no interferent bias due to the acetaminophen, but would show some interferent bias if the sample included dopamine.

Figure 11C:
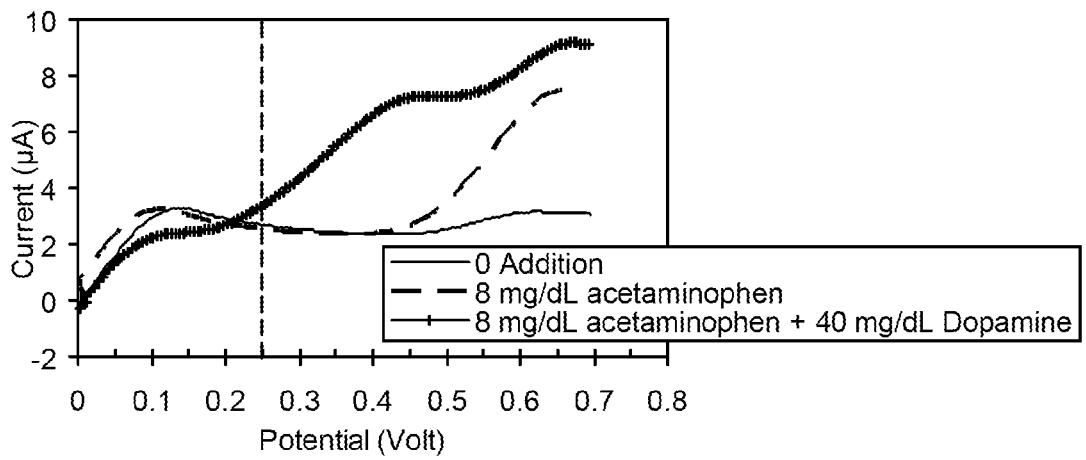
FIG. 11C provides an expansion of the output currents from the linear scan of the third duty cycle of FIG. 11A.

FIG. 11C plots the output currents verses potential for the linear scan of duty cycle 3 from FIG. 11A. The dashed vertical line indicates the 0.25 V potential used for the amperometric excitations of duty cycles 4, 5, and 7. For the sample including the additional acetaminophen, output currents obtained substantially overlap with those obtained from the 0 addition sample until about 0.45 V—well beyond the 0.25 V potential of the amperometric excitation of duty cycle 7. In contrast, for the sample including additional acetaminophen and dopamine, the onset of output currents attributable to dopamine were observed at about 0.22 V, thus within the output currents obtained at the 0.25 V potential of the amperometric excitation of duty cycle 7. As previously described with regard to FIG. 11B, some interferent bias from dopamine would be present in a glucose concentration determined from output currents obtained from a 0.25 V amperometric excitation.

Figure 11D:
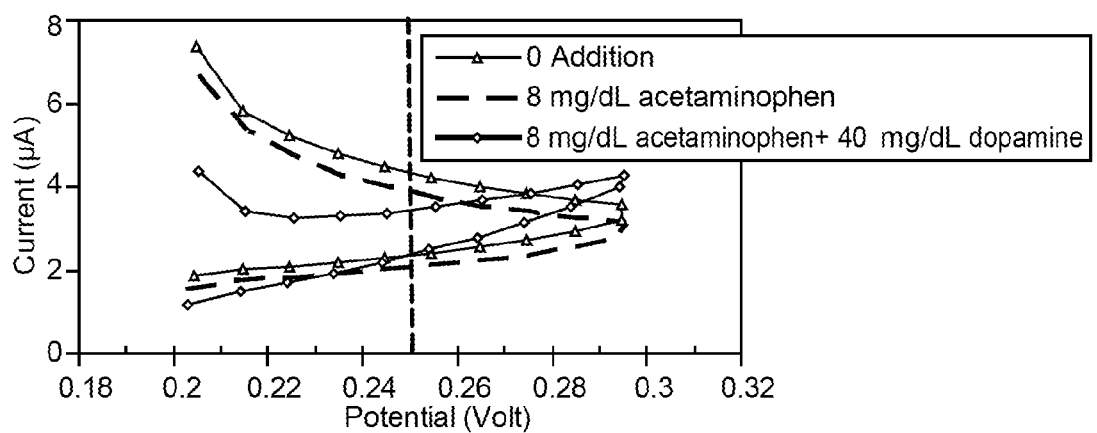
FIG. 11D plots the output currents versus potential from the duty cycle 8 acyclic scan for the three samples.

FIG. 11D plots the output currents versus potential from the duty cycle 6 acyclic scan for the three samples. While the output currents from the forward excitation of the acyclic scans for the 0 addition sample and the sample including additional acetaminophen show a continuing decrease, the current values from the sample with additional acetaminophen and dopamine initially decrease and then increase. Thus, the forward excitation of the acyclic scan shows the presence of output currents responsive to a second contributing ionizable species, in this case the dopamine interferent, within the about 0.2 V to about 0.3 V scan range from the initial down and then up output current values. The system can detect the presence of additional ionizable species contributing to the output currents within the range of the forward excitation of an acyclic scan from the inflection in the current values.

Ratios provide one method to determine the presence of one or more contributing ionizable species from the output currents of the acyclic scans. A first ratio may be determined from the initial and the midpoint output current values of the forward acyclic scan ($R_1$=initial output current/midpoint output current). A second ratio may be determined from the midpoint and the reversing point output currents of the forward acyclic scan ($R_2$=midpoint output current/reversing point output current). If the two ratios are greater than one, then one contributing ionizable species is present. Conversely, if the first ratio is greater than one and the second ratio is less than one, at least two contributing ionizable species are present. In addition to ratios, other techniques may be used to compare the output currents obtained from the acyclic scan duty cycles, such as derivatives, integrals, pattern recognition methods, and the like, to determine if more than one ionizable species is observed by the acyclic scan.

In the FIG. 11D acyclic scans, the output currents from the sample lacking acetaminophen and dopamine interferents have a first ratio of 1.65 (7.36/4.47 uA) and a second ratio of 1.26 (4.47/3.54 uA). As both ratios are greater than one, the presence of a single contributing ionizable species, in this case the mediator, is indicated. The first and second ratios for the output currents from the sample including acetaminophen as an interferent also are both greater than one. As both ratios are greater than one, the presence of a single contributing ionizable species, again the mediator, is indicated. As confirmed in FIG. 11B and FIG. 11C, additional acetaminophen has little if any effect on the bias of the analyte concentration determined using amperometric excitations at a potential of 0.25 V. The output currents from the sample including acetaminophen and dopamine have a first ratio of 1.26 (4.35/3.37 uA) and a second ratio of 0.79 (3.37/4.27 uA). As the second ratio is less than one, at least two contributing ionizable species are present. Thus, output currents recorded over a scan range from 0.2 V to 0.3 V would provide a glucose concentration including a bias from dopamine.

As the acyclic scan establishes that two contributing ionizable species are present in the 0.2 V to 0.3 V scan range, the maximum potential of subsequent acyclic scans may be reduced until the second ratio increases above one, thus reducing output currents responsive to the dopamine interferent and the interferent bias present in the glucose concentration. As previously discussed, the linearity of the output current values may be monitored as the potentials are reduced to select an acyclic scan range or amperometric excitation potential that balances the negative effects of non-linear response and interferent bias. Acyclic scans may be preferred to determine the presence and/or potentials of one or more contributing ionizable species. Amperometric excitations may be preferred to provide output current values with reduced non-linearity and interferent bias for concentration determination. As amperometric excitations are applied at a substantially constant, single potential, the single potential value of the amperometric excitations has a greater likelihood of being low enough to reduce output currents responsive to interferents while being high enough to reduce non-linearity. Any combination of linear or acyclic scans may be used to determine the presence and/or potentials of the contributing ionizable species and/or the non-linearity of the output currents at a potential or a potential range.

Figure 12A:
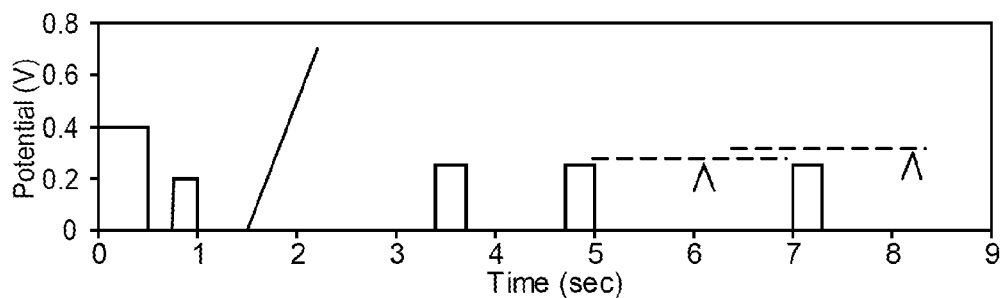
FIG. 12A represents an input signal having a total of eight duty cycles, where duty cycles 1, 2, 4, 5, and 7 have amperometric excitations, duty cycle 3 has a linear scan, and duty cycles 6 and 8 have acyclic scans.

FIG. 12A represents an input signal having a total of eight duty cycles, where duty cycles 1, 2, 4, 5, and 7 have amperometric excitations, duty cycle 3 has a linear scan, and duty cycles 6 and 8 have acyclic scans. The amperometric excitations for duty cycles 4, 5, and 7 were applied at a voltage of about 0.25 V. The linear scan rate was about 1 V/sec from 0 to about 0.7 V. The acyclic scan of duty cycle 6 had a scan rate of about 1 V/sec from about 0.15 V to about 0.25 V and back. The acyclic scan of duty cycle 8 had a scan rate of about 1 V/sec from about 0.2 V to about 0.3 V and back. Other input signals having different numbers and types of duty cycles, potentials, and scan rates may be used. For example, a cyclic scan could be substituted for the linear scan.

Figure 12B:
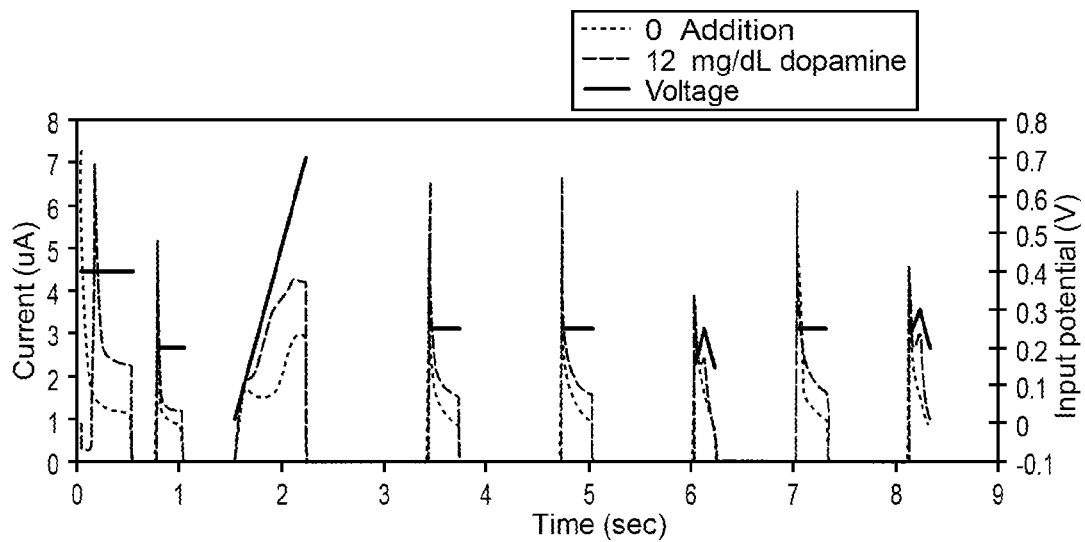
FIG. 12B plots the output currents as a function of time obtained when a measurement device applied the input signal of FIG. 12A to sensor strips including plasma, about 66 mg/dL of glucose as the analyte, and either no additional interferents or about 12 mg/dL dopamine.

FIG. 12B plots the obtained output currents as a function of time when a measurement device applied the input signal of FIG. 12A to sensor strips including plasma, about 66 mg/dL of glucose as the analyte, and either no additional interferents or about 12 mg/dL of dopamine. Other analytes and interferents may be used. The sensor strip included working and counter electrodes, glucose dehydrogenase as an oxidoreductase, and the organic two electron mediator of Structure I. Other sensor strip designs and reagents may be used.

Figure 12C:
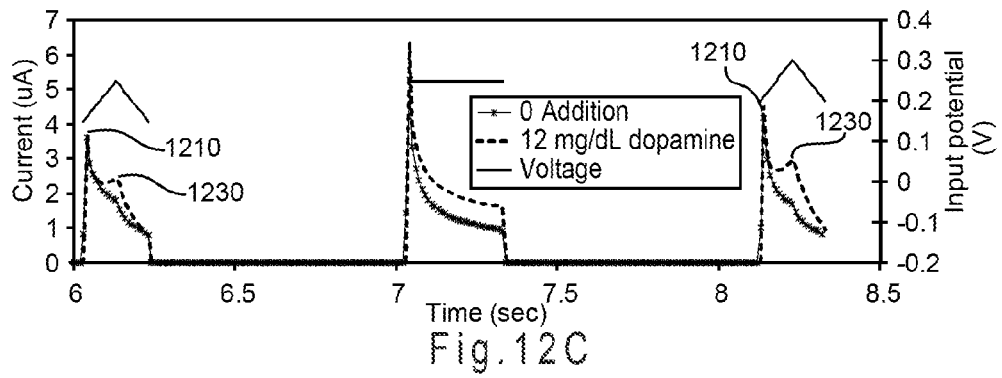
FIG. 12C provides expansions of the output currents recorded from the acyclic scans of duty cycles 6 and 8 and from the amperometric excitation of duty cycle 7.

FIG. 12C provides expansions of the output currents recorded from the acyclic scans of duty cycles 6 and 8 and from the amperometric excitation of duty cycle 7. As seen by dopamine peaks 1230 (the mediator is peaks 1210), the acyclic scan of duty cycle 6 at the lower 0.15 to 0.25 V potential includes less current responsive to dopamine than the acyclic scan of duty cycle 8 at the higher 0.2 V to 0.3 V potential. The 0.25 V potential of the amperometric excitation of duty cycle 7 produced output currents including dopamine as seen in the middle peak, thus reducing the accuracy of an analyte concentration determined from these output currents (an approximately 15% to 20% positive bias in the glucose concentration determined from the output currents of the amperometric scan is estimated from the dopamine interferent). This would be expected from a 0.25 V input potential in view of the output currents obtained from the acyclic scans.

Figure 12D:
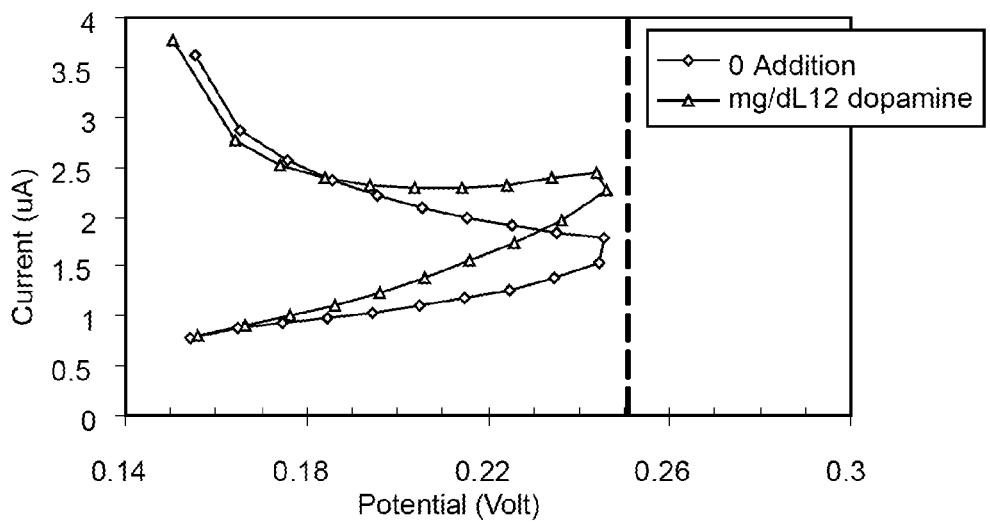
FIG. 12D and FIG. 12E plot the output currents versus potential from the duty cycle 6 and 8 acyclic scans for two samples.
Figure 12E:
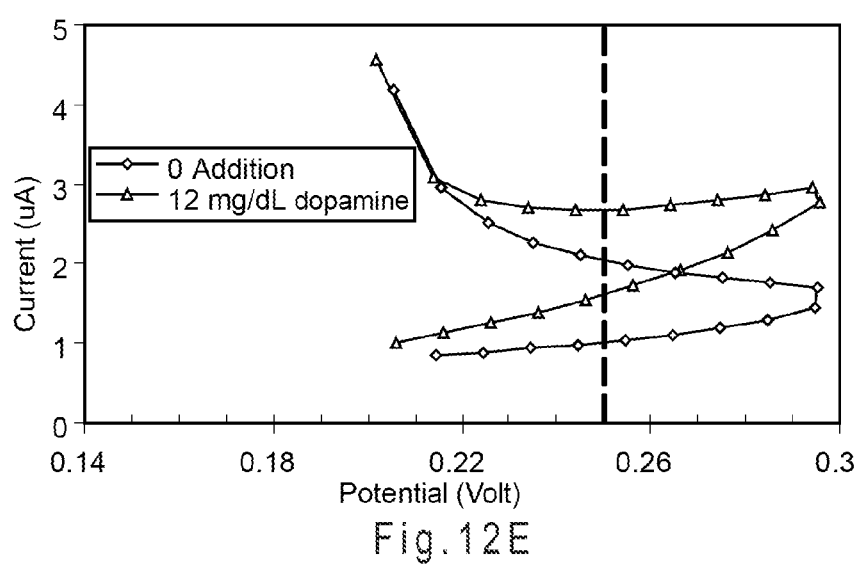

FIG. 12D and FIG. 12E plot the output currents versus potential from the duty cycle 6 and 8 acyclic scans for the two samples. As previously discussed, ratios may be used to determine the presence of one or more contributing ionizable species from the output currents of the acyclic scans. From the lower potential acyclic scans of FIG. 12D, the output currents from the sample lacking dopamine have a first ratio of 1.65 (3.6/2.2 uA) and a second ratio of 1.22 (2.2/1.79 uA). As both ratios are greater than one, the presence of a single contributing ionizable species, in this case the mediator, is indicated. The output currents from the sample including dopamine have a first ratio of 1.63 (3.77/2.31 uA) and a second ratio of 0.95 (2.31/2.43 uA). As the second ratio is less than one, the presence of a second contributing ionizable species, in this case the dopamine interferent, is indicated. However, the second ratio of 0.95 is nearly one, indicating that for the 0.15 V to 0.25 V potential range the interferent influence on the analysis is relatively minimal. Thus, the 0.15 V to 0.25 V potential range may be selected for amperometric excitations if this range provides the ratio closest to one of the potentials scanned.

In FIG. 12E, from the 0.2 to 0.3 V potential scans, the output currents from the sample lacking dopamine have a first ratio of 1.99 (4.18/2.1 uA) and a second ratio of 1.23 (2.1/1.7 uA). As both ratios are greater than one, the presence of a single contributing ionizable species, in this case the mediator, is indicated. The output currents from the sample including dopamine as an interferent have a first ratio of 1.7 (4.56/2.67 uA) and a second ratio of 0.91 (2.67/2.95 uA). As the second ratio is less than one, the presence of a second contributing ionizable species, in this case the dopamine interferent, is indicated. When the second ratio of the higher potential acyclic scan (0.91) is compared to the second ratio of the lower potential acyclic scan (0.95), the potential of the amperometric excitation may be selected from the lower potential scan range, as the lower potential more effectively excludes output currents responsive to the dopamine interferent.

Figure 12F:
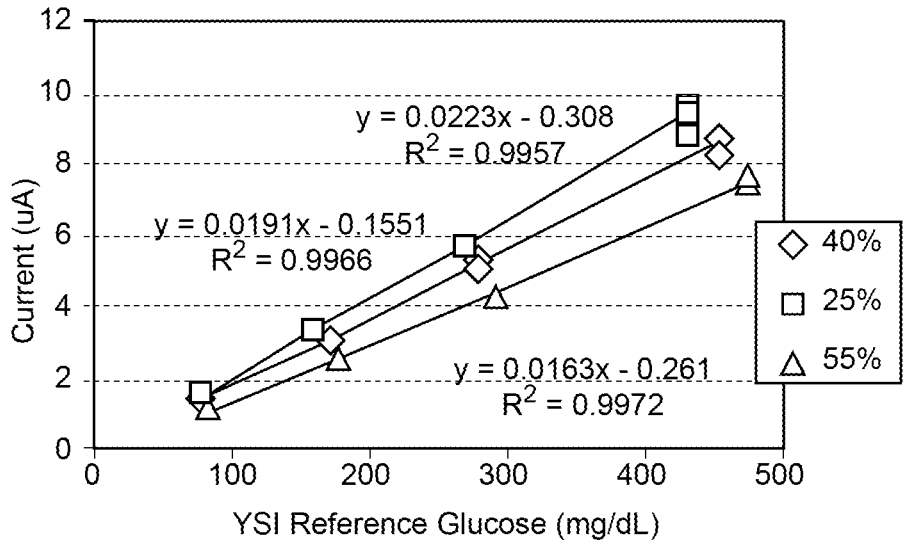
FIG. 12F plots the dose response of current as a function of the glucose concentrations determined for each sample from a single output current.
Figure 12G:
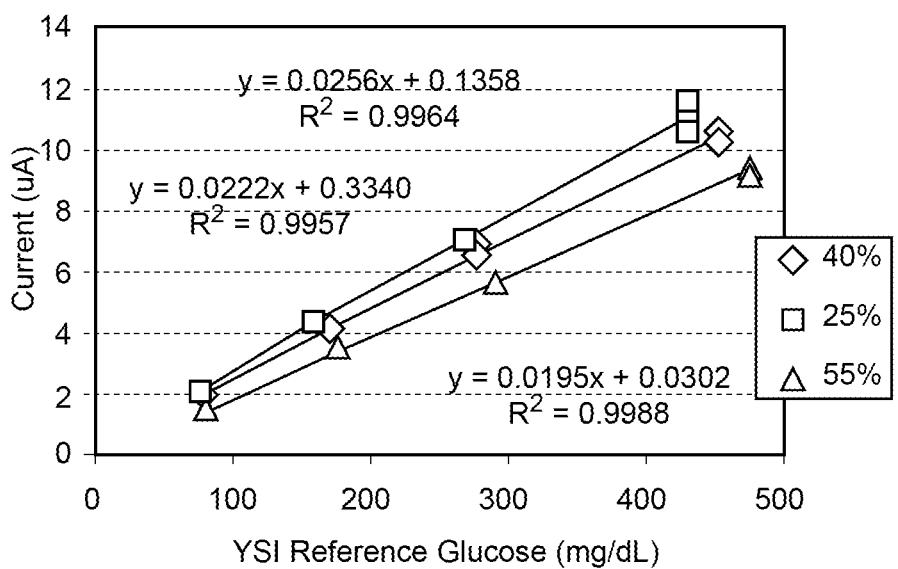
FIG. 12G plots the dose response of current as a function of the glucose concentrations determined for each sample by averaging output currents.

The input signal of FIG. 12A also was applied to whole blood samples including multiple known concentrations of glucose at hematocrit levels of 25%, 40%, or 55% (v/v). A YSI reference instrument was used to determine the reference (known) glucose concentration of each sample. FIG. 12F plots the dose response of a single output current as a function of the known glucose concentrations for each sample. The single output current was taken from the amperometric excitation of duty cycle 5. FIG. 12G plots the dose response of averaged output currents as a function of the known glucose concentrations for each sample. The averaged output currents were determined by averaging the output currents obtained from the acyclic scan of duty cycle 6.

As seen below in Table III, a slight increase was observed in the $R^2$ of the concentration values when the averaged output currents were compared to the single output current. Thus, the glucose concentrations determined from averaging the output currents from the acyclic scan were comparable to the glucose concentrations determined from a single output current from the acyclic scan. The averaged output currents from the acyclic scan provided some increase in the sensitivity of the system as observed from the increase in the slope values of the correlation lines. Increases in the numerical value of the slope reflect an increase in the correlation between the output currents and the actual analyte concentration of the sample. Thus, analyte concentrations can be determined from single output currents and/or from output currents combined through averaging and the like. The single or averaged output current values may be used to determine the concentration of one or more analytes in the sample using one or more data treatments and/or correlation equations. While the preceding description addresses input signals including amperometric and at least one voltammetric duty cycle, the amperometric excitation could be substituted with an acyclic scan from which the analyte concentration also may be determined. Thus, the input signal does not require an amperometric duty cycle. Additional information regarding the determination of analyte concentrations from gated voltammetric input signals may be found in U.S. Patent Doc. 2008/0179197, entitled "Gated Voltammetry."

TABLE III

|  | 25% Hematocrit | 40% Hematocrit | 55% Hematocrit |
| --- | --- | --- | --- |
| Single Current $R^2$ | 0.9957 | 0.9966 | 0.9972 |
| Single Current Slope | 0.0223 | 0.0191 | 0.0163 |
| Averaged Currents $R^2$ | 0.9964 | 0.9957 | 0.9988 |
| Averaged Currents Slope | 0.0256 | 0.0222 | 0.0195 |

While not shown in the figures, if the system determines from the output currents obtained from the voltammetric scans that more than one contributing ionizable species is present in the sample, the system can reduce the scan rate of a voltammetric scan to better define the output currents. For example, if closely spaced peaks are present in the output currents from a linear scan, the scan rate could be reduced from 1 V/sec to 0.5 V/sec to increase the output current resolution in the potential range of interest. Other scan rates may be selected.

Figure 13:
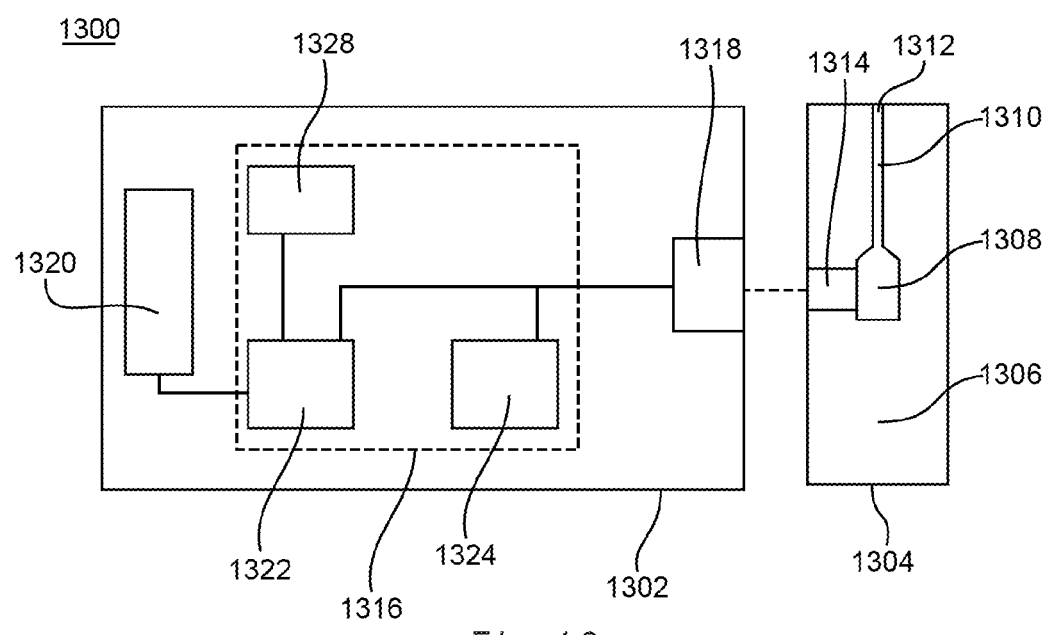
FIG. 13 depicts a schematic representation of a biosensor system that determines an analyte concentration in a sample.

FIG. 13 depicts a schematic representation of a biosensor system 1300 that determines an analyte concentration in a sample of a biological fluid using an input signal including amperometric and at least one voltammetric duty cycle. The input signal may lack the amperometric duty cycle when at least one acyclic scan duty cycle is applied to the sample. Biosensor system 1300 includes a measurement device 1302 and a sensor strip 1304, which may be implemented in any analytical instrument, including a bench-top device, a portable or hand-held device, or the like. The biosensor system 1300 may be utilized to determine analyte or interferent concentrations, including those of alcohol, glucose, uric acid, lactate, cholesterol, bilirubin, free fatty acids, triglycerides, proteins, ketones, phenylalanine, enzymes, acetaminophen, dopamine, and the like. While a particular configuration is shown, the biosensor system 1300 may have other configurations, including those with additional components.

Measurement device 1302 and sensor strip 1304 may be adapted to implement an electrochemical sensor system or a combination electrochemical/optical sensor system. The combined amperometric and voltammetric duty cycles may improve the accuracy and/or precision of the biosensor system 1300 by reducing output currents obtained from interferents, or may allow the biosensor system 1300 to determine the concentration of more than one ionizable species. While a particular configuration is shown, biosensor system 1300 may have other configurations, including those with additional components.

The sensor strip 1304 has a base 1306 that forms a reservoir 1308 and a channel 1310 with an opening 1312. The reservoir 1308 and the channel 1310 may be covered by a lid with a vent. The reservoir 1308 defines a partially-enclosed volume. The reservoir 1308 may contain a composition that assists in retaining a liquid sample such as water-swellable polymers or porous polymer matrices. Reagents may be deposited in the reservoir 1308 and/or channel 1310. The reagents may include one or more enzymes, enzyme systems, mediators, binders, and like species. The sensor strip 1304 also may have a sample interface 1314 disposed adjacent to the reservoir 1308. The sample interface 1314 may partially or completely surround the reservoir 1308. The sensor strip 1304 may have other configurations. For example, the sensor strip 1304 may be adapted for transdermal use by forming the reservoir 1308 from a porous material or behind a porous material in which the sample is held.

The sample interface 1314 has conductors connected to at least one working electrode and at least one counter electrode. The electrodes may be substantially in the same plane or in more than one plane, such as when facing. The electrodes may be disposed on a surface of the base 1306 that forms the reservoir 1308. The electrodes may extend or project into the reservoir 1308. A dielectric layer may partially cover the conductors and/or the electrodes. The counter electrode may be used to balance the potential at the working electrode during the analysis. The balancing potential may be provided by forming the counter electrode from an inert material, such as carbon, and including a soluble redox species, such as ferricyanide, within the reservoir 1308. Alternatively, the balancing potential may be a reference potential achieved by forming the counter electrode from a reference redox couple, such as Ag/AgCl, to provide a combined reference-counter electrode. The sample interface 1314 may have other electrodes and conductors. Sample interface 1314 may have one or more optical portals or apertures for viewing the sample. Sample interface 1314 may have other components and configurations.

The measurement device 1302 includes electrical circuitry 1316 connected to a sensor interface 1318 and a display 1320. The electrical circuitry 1316 includes a processor 1322 connected to a signal generator 1324, and a storage medium 1328. Measurement device 1302 may have other components and configurations.

The signal generator 1324 provides an electrical input signal to the sensor interface 1318 in response to the processor 1322. The electrical input signal may be transmitted by the sensor interface 1318 to the sample interface 1314 to apply the electrical input signal to the sample of the biological fluid. The electrical input signal may be a potential or current and may be constant, variable, or a combination thereof, such as when an AC signal is applied with a DC signal offset. The electrical input signal may be applied as a single pulse or in multiple pulses, sequences, or cycles. The electrical input signal may include amperometric and at least one voltammetric duty cycle. The electrical input signal may lack an amperometric duty cycle when at least one acyclic scan duty cycle is applied to the sample. The electrical input signal may include at least three amperometric and at least two acyclic scan duty cycles. The signal generator 1324 also may record an output signal from the sensor interface as a generator-recorder.

The storage medium 1328 may be a magnetic, optical, or semiconductor memory, another processor readable storage device, or the like. The storage medium 1328 may be a fixed memory device, a removable memory device, such as a memory card, remotely accessed, or the like.

The processor 1322 implements the analyte analysis using computer readable software code and data stored in the storage medium 1328. The processor 1322 may start the analyte analysis in response to the presence of the sensor strip 1304 at the sensor interface 1318, the application of a sample to the sensor strip 1304, in response to user input, or the like. The processor 1322 directs the signal generator 1324 to provide the electrical input signal to the sensor interface 1318.

The processor 1322 receives the output signal from the sensor interface 1318. The output signal is generated in response to the redox reaction of the ionizable species in the sample. The processor 1322 measures the output signal responsive to the amperometric and/or voltammetric duty cycles of the input signal generated from the signal generator 1324. The processor 1322 analyzes the output currents from one or more voltammetric inputs to determine if one or more interferents are present in the sample and/or if non-linear response is occurring. The processor 1322 then may instruct the signal generator 1324 to adjust the potential and/or the scan rate of one or more amperometric or voltammetric duty cycles.

The output signal from the adjusted input signal is correlated with the concentration of at least one ionizable species in the sample using one or more correlation equations in the processor 1322. The processor 1322 may correct the concentration of one ionizable species with the concentration of another ionizable species. The results of the analyte analysis may be output to the display 1320 and may be stored in the storage medium 1328.

The correlation equations between ionizable species and output signals may be represented graphically, mathematically, a combination thereof, or the like. The correlation equations may be represented by a program number (PNA) table, another look-up table, or the like that is stored in the storage medium 1328. Instructions regarding implementation of the analysis may be provided by the computer readable software code stored in the storage medium 1328. The code may be object code or any other code describing or controlling the functionality described herein. The data from the analysis may be subjected to one or more data treatments, including the determination of decay rates, K constants, ratios, and the like in the processor 1322.

The sensor interface 1318 has contacts that connect or electrically communicate with the conductors in the sample interface 1314 of the sensor strip 1304. The sensor interface 1318 transmits the electrical input signal from the signal generator 1324 through the contacts to the connectors in the sample interface 1314. The sensor interface 1318 also transmits the output signal from the sample through the contacts to the processor 1322 and/or signal generator 1324.

The display 1320 may be analog or digital. The display 1320 may be a LCD, a LED, an OLED, a vacuum fluorescent, or other display adapted to show a numerical reading. Other displays may be used. The display 1320 electrically communicates with the processor 1322. The display 1320 may be separate from the measurement device 1302, such as when in wireless communication with the processor 1322. Alternatively, the display 1320 may be removed from the measurement device 1302, such as when the measurement device 1302 electrically communicates with a remote computing device, medication dosing pump, and the like.

In use, a liquid sample for analysis is transferred into the reservoir formed by the reservoir 1308 by introducing the liquid to the opening 1312. The liquid sample flows through the channel 1310, filling the reservoir 1308 while expelling the previously contained air. The liquid sample chemically reacts with the reagents deposited in the channel 1310 and/or reservoir 1308.

The following definitions are included to provide a clear and consistent understanding of the specification and claims.

The term "linear scan" is defined as a voltammetric excitation where the voltage is varied in a single "forward" direction at a fixed rate, such as from −0.5 V to +0.5 V to provide a 1.0 V scan range. The scan range may cover the reduced and oxidized states of a redox couple so that a transition from one state to the other occurs. A linear scan may be continuous or may be approximated by a series of incremental changes in potential. If the increments occur very close together in time, they correspond to a continuous linear scan. Thus, applying a change of potential approximating a linear change may be considered a linear scan.

The term "cyclic scan" is defined as a voltammetric excitation combining a linear forward scan and a linear reverse scan, where the scan range includes the oxidation and reduction peaks of a redox couple. For example, varying the potential in a cyclic manner from −0.5 V to +0.5 V and back to −0.5 V is an example of a cyclic scan for the ferricyanide/ferrocyanide redox couple as used in a glucose sensor, where both the oxidation and reduction peaks are included in the scan range. Both the forward and reverse scans may be approximated by a series of incremental changes in potential. Thus, applying a change of potential approximating a cyclic change may be considered a cyclic scan.

The term "acyclic scan" is defined in one aspect as a voltammetric excitation including more of one forward or reverse current peak than the other current peak. For example, a scan including forward and reverse linear scans where the forward scan is started at a different voltage than where the reverse scan stops, such as from −0.5 V to +0.5 V and back to +0.25 V, is an example of an acyclic scan. In another example, an acyclic scan may start and end at substantially the same voltage when the scan is started at most ±20, ±10, or ±5 mV away from the formal potential $E^{o\prime}$ of a redox couple. In another aspect, an acyclic scan is defined as a voltammetric excitation including forward and reverse linear scans that substantially exclude the oxidation and reduction output current peaks of a redox couple. For example, the excitation may begin, reverse, and end within the DLC region of a redox couple, thus excluding the oxidation and reduction output current peaks of the couple. Both the forward and reverse scans may be approximated by a series of incremental changes in potential. Thus, applying a change of potential approximating an acyclic change may be considered an acyclic scan.

The terms "fast scan" and "fast scan rate" are defined as a scan where the voltage is changed at a rate of at least 176 mV/sec. Preferable fast scan rates are rates greater than 200, 500, 1,000, or 2,000 mV/sec.

The terms "slow scan" and "slow scan rate" are defined as a scan where the voltage is changed at a rate of at most 175 mV/sec. Preferable slow scan rates are rates slower than 150, 100, 50, or 10 mV/sec.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method for identifying and/or measuring an ionizable species in a sample, the method comprising:
  applying an electric input signal to the sample, the electric input signal including a plurality of duty cycles, each duty cycle of the plurality of duty cycles including:
    exciting the sample with an electrical pulse during an excitation period; and
    relaxing the sample after the electrical pulse during a relaxation period;
  detecting an output signal of the sample responsive to the electric input signal;
  adjusting the electric input signal based on the output signal responsive to at least one duty cycle; and
  identifying and/or measuring the ionizable species in the sample based on the output signal.

2. The method of claim 1, wherein an electric current of the electric input signal is reduced to at least one-half of an electric current at an excitation maximum during the relaxation periods.

3. The method of claim 1, wherein an electric current of the electric input signal is reduced by at least an order of magnitude relative to an electric current at an excitation maximum during the relaxation periods.

4. The method of claim 1, wherein an electric current to the sample is reduced to a zero electric current state during the relaxation periods.

5. The method of claim 4, wherein the electric input signal is applied to the sample through an electric circuit including at least one working electrode and at least one counter electrode at a sensor strip containing the sample, the method further comprising:
  opening the electric circuit to provide the zero electric current state.

6. The method of claim 1, wherein the plurality of duty cycles of the electric input signal includes at least three duty cycles.

7. The method of claim 1, wherein the plurality of duty cycles of the electric input signal is applied within about 30 seconds.

8. The method of claim 1, wherein the plurality of duty cycles of the electric input signal includes at least four duty cycles applied within about seven seconds.

9. The method of claim 1, wherein each excitation period of the plurality of duty cycles is about 0.3 to 0.8 seconds long.

10. The method of claim 1, wherein each duty cycle of the plurality of duty cycles has a length of less than three seconds.

11. The method of claim 1, wherein each excitation period of the plurality of duty cycles is about 0.3 to 0.5 seconds long, and each duty cycle of the plurality of duty cycles has an interval of less than two seconds.

12. The method of claim 1,
wherein the at least one duty cycle includes a voltammetric pulse.

13. The method of claim 1, wherein at least one electrical pulse of the electrical pulses is a linear voltammetric pulse, a cyclic voltammetric pulse, or an acyclic voltammetric pulse.

14. The method of claim 13, wherein the at least one electrical pulse is an acyclic voltammetric pulse that includes a larger forward or reverse current peak than the other of the forward or reverse current peak.

15. The method of claim 13, wherein the at least one electrical pulse is an acyclic voltammetric pulse that starts and ends at substantially a same voltage when started at most 20 millivolts away from a formal potential $E^{0'}$ of a redox couple of the sample.

16. The method of claim 13, wherein the at least one electrical pulse is an acyclic voltammetric pulse that includes a forward and a reverse increase in voltage that substantially exclude oxidation and reduction output current peaks of a redox couple of the sample.

17. The method of claim 13, wherein the at least one electrical pulse is a linear voltammetric pulse that includes an increase in voltage at a fixed rate.

18. The method of claim 13, wherein the at least one electrical pulse is a cyclic voltammetric pulse that includes an increase and a decrease in voltage at a fixed rate and includes oxidation and reduction peaks of a redox couple of the sample.

19. The method of claim 13, wherein a preceding or a following electrical pulse to the at least one electrical pulse is an amperometric pulse.

20. The method of claim 1, wherein the identifying and/or measuring of the ionizable species in the sample is based on the output signal responsive to the excitation periods.

* * * * *